US008962546B2

(12) United States Patent
Narkar et al.

(10) Patent No.: US 8,962,546 B2
(45) Date of Patent: Feb. 24, 2015

(54) MODULATION OF ESTROGEN RECEPTOR-RELATED RECEPTOR GAMMA (ERRγ) AND USES THEREFOR

(75) Inventors: Vihang A. Narkar, Houston, TX (US); Michael Downes, San Diego, CA (US); Ruth T. Yu, La Jolla, CA (US); Ronald M. Evans, La Jolla, CA (US)

(73) Assignee: Salk Institute for Biological Studies, La Jolla, CA (US)

(*) Notice: Subject to any disclaimer, the term of this patent is extended or adjusted under 35 U.S.C. 154(b) by 0 days.

(21) Appl. No.: 13/410,142

(22) Filed: Mar. 1, 2012

(65) Prior Publication Data

US 2012/0302491 A1    Nov. 29, 2012

Related U.S. Application Data

(60) Provisional application No. 61/447,704, filed on Mar. 1, 2011.

(51) Int. Cl.
| | |
|---|---|
| *A61K 31/16* | (2006.01) |
| *A61P 21/00* | (2006.01) |
| *A61P 25/00* | (2006.01) |
| *A61P 9/00* | (2006.01) |
| *A61K 31/166* | (2006.01) |
| *A61K 38/17* | (2006.01) |
| *A61K 48/00* | (2006.01) |

(52) U.S. Cl.
CPC ............ *A61K 31/166* (2013.01); *A61K 38/177* (2013.01); *A61K 48/00* (2013.01)
USPC ............................ 514/1.1; 514/615; 514/616

(58) Field of Classification Search
CPC ... A61K 31/166; A61K 38/177; A61K 48/00; A61K 38/17
USPC ......................................... 514/1.1, 44 R, 615
See application file for complete search history.

(56) References Cited

U.S. PATENT DOCUMENTS

| | | | | |
|---|---|---|---|---|
| 5,595,756 | A * | 1/1997 | Bally et al. ................... | 424/450 |
| 7,544,838 | B2 | 6/2009 | Forman et al. | |
| 8,044,241 | B2 | 10/2011 | Forman et al. | |
| 2009/0281191 | A1 * | 11/2009 | Rangwala et al. ............ | 514/615 |
| 2011/0071148 | A1 | 3/2011 | Ding et al. | |
| 2011/0218196 | A1 | 9/2011 | Ding et al. | |

FOREIGN PATENT DOCUMENTS

| | | |
|---|---|---|
| WO | WO 2007/130431 A2 | 11/2007 |
| WO | WO 2007/131005 A2 | 11/2007 |
| WO | WO 2009/021022 A2 | 2/2009 |

OTHER PUBLICATIONS

Jefferson C. Frisbee, Exercise training blunts microvascular rarefaction in the metabolic syndrome, 2006, Am J. Physiol, vol. 291:2483-2492.*
Johnathan M. Peterson, 2008, Satellite Cell proliferation is reduced in mucles of obese Zucker rats but restored with loading, Am J. Physiol, vol. 295:521-528.*
Manuela Aragno, Oxidative Stress Impairs Skeletal Muscle Repair in Diabetic Rats, 2004, Diabetes, vol. 53:1082-1088.*
Katie Watts, Exercise training normalizes vascular dysfunction and improves central obesity in obese adolescents, 2004, JACC, 43:1823-1827.*
A Efthimiadou, Angiogenic effect of intramuscular administration of basic fibroblast growth factor in atrophied muscles: an experimental study in the rat, Br. J. Sports Med, 2006, vol. 40:355-358.*
Michael B. Sporn, Chemoprevention of cancer,2000, Carcinogenesis, vol. 21 No. 3, pp. 535-530.*
Trisha Gura, Systems for Identifying New Drugs are Often Faulty, 1997, Science, vol. 278 No. 5340, pp. 1041-1042.*
Robert Auerbach, Angiogenesis assays: Problems and Pitfalls, 2000, Cancer and Metastasis Reviews, vol. 19, pp. 167-172.*
Stephen Neidle, Cancer Drug Design and Discovery, 2008, Elsevier/Academic Press, pp. 427-431.*
Rakesh K. Jain, Barriers to Drug Delivery in Solid Tumors, 1994, Scientific Journal, pp. 58-65.*
Kim et al., "Efficient Discovery of Selective Small Molecule Agonists of Estrogen-Related Receptor γ using Combinatorial Approach," *J. Comb. Chem.* 11:928-937, 2009.
Narkar et al., "Exercise and PGC-1α-Independent Synchronization of Type I Muscle Metabolism and Vasculature by ERRγ," *Cell Metabolism* 13:283-293, 2011.
Rangwala et al., "Estrogen-Related Receptor γ Is a Key Regulator of Muscle Mitochondrial Activity and Oxidative Capacity," *J. Biol. Chem.* 285:22619-22629, 2010.

* cited by examiner

*Primary Examiner* — James H Alstrum Acevedo
*Assistant Examiner* — Erinne Dabkowski
(74) *Attorney, Agent, or Firm* — Klarquist Sparkman, LLP

(57) ABSTRACT

This application provides methods of increasing vascularization, muscle performance, muscle rehabilitation, and/or mitochondrial activity in subjects in need thereof, by administering a therapeutically effective amount of one or more agents that increases ERRγ activity to the subject. Such agents can include one or more ERRγ agonists. In some examples the method does not require that the subject exercise, and as such, the subject may be sedentary (such as bedridden or in a wheelchair).

18 Claims, 10 Drawing Sheets

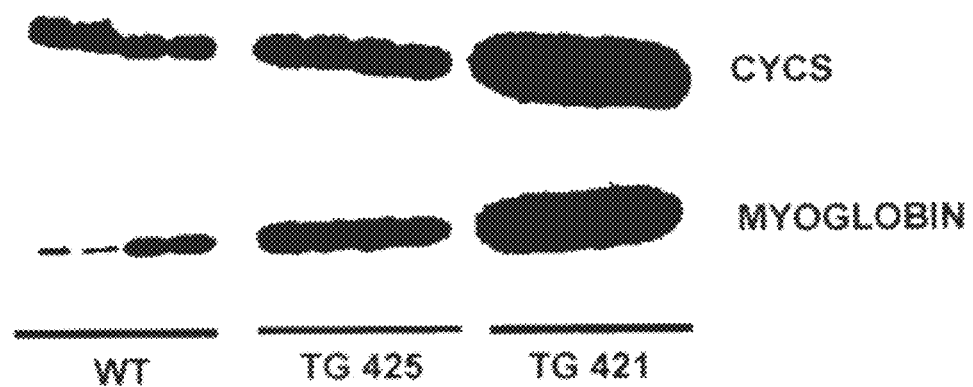

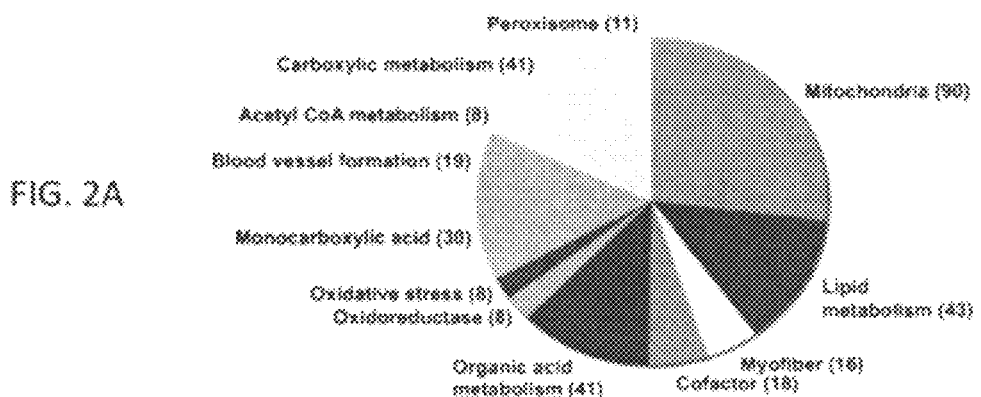
FIG. 2A
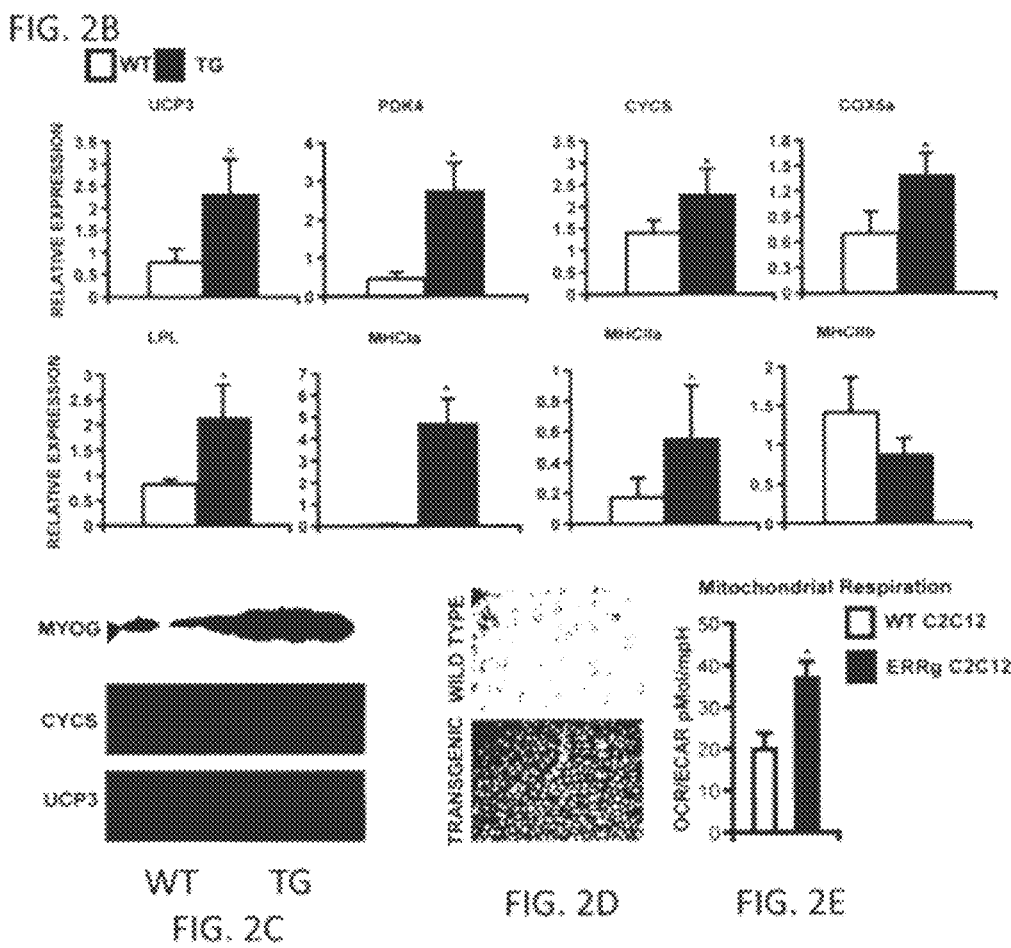
FIG. 2B
FIG. 2C
FIG. 2D
FIG. 2E

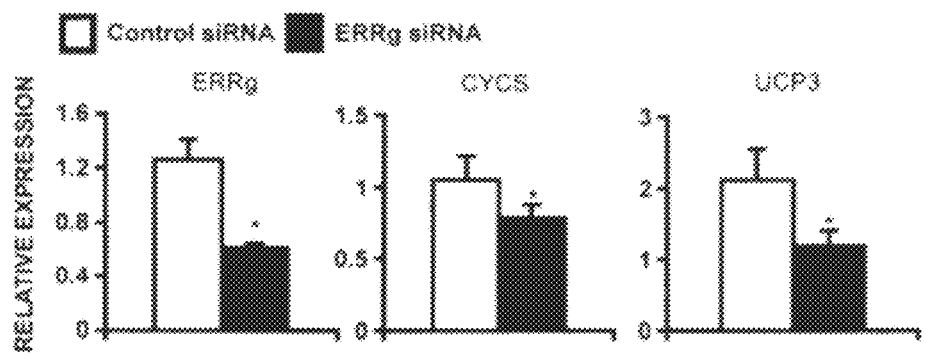
FIG. 2F
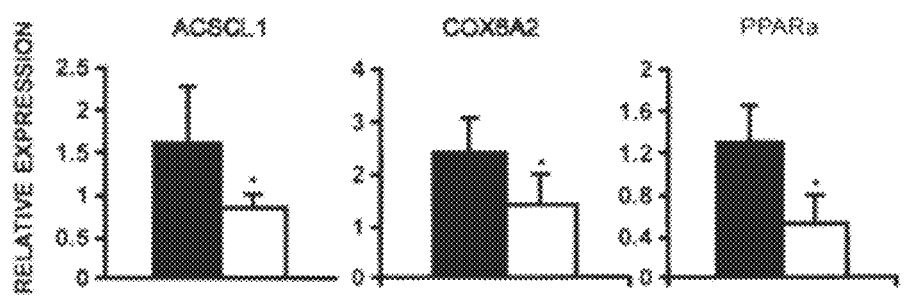
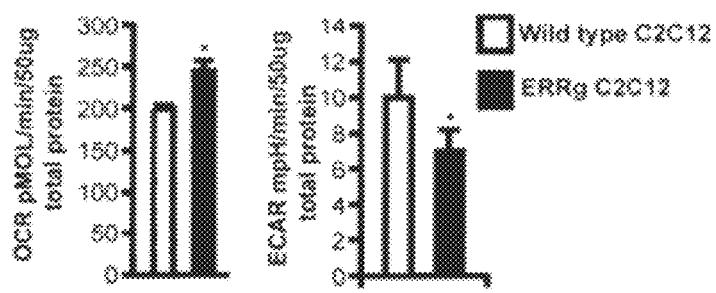
FIG. 2G  FIG. 2H

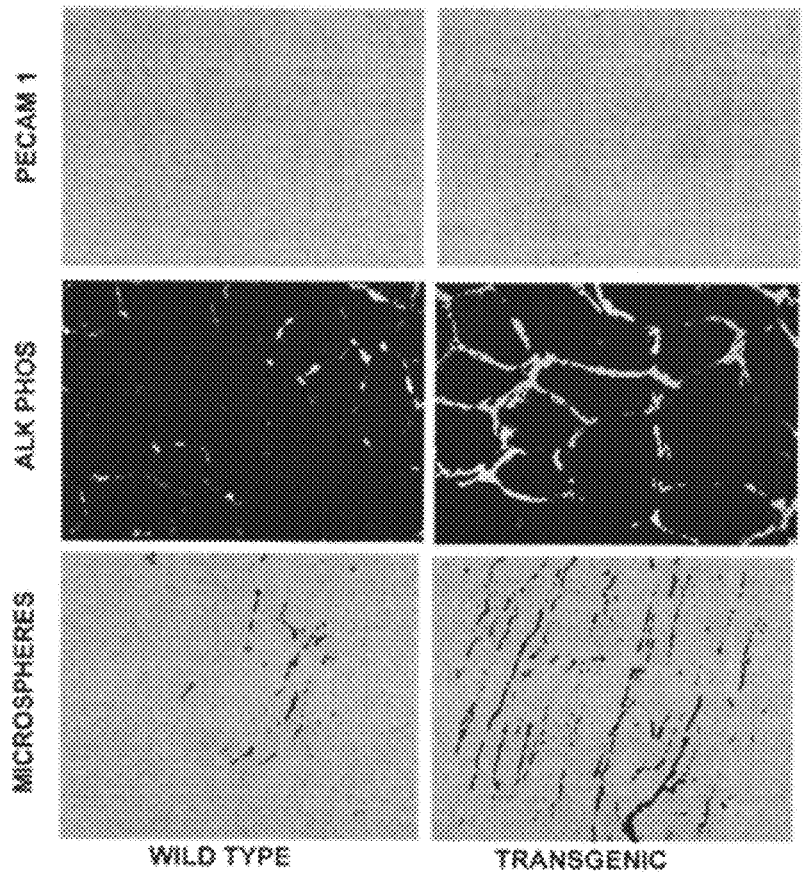
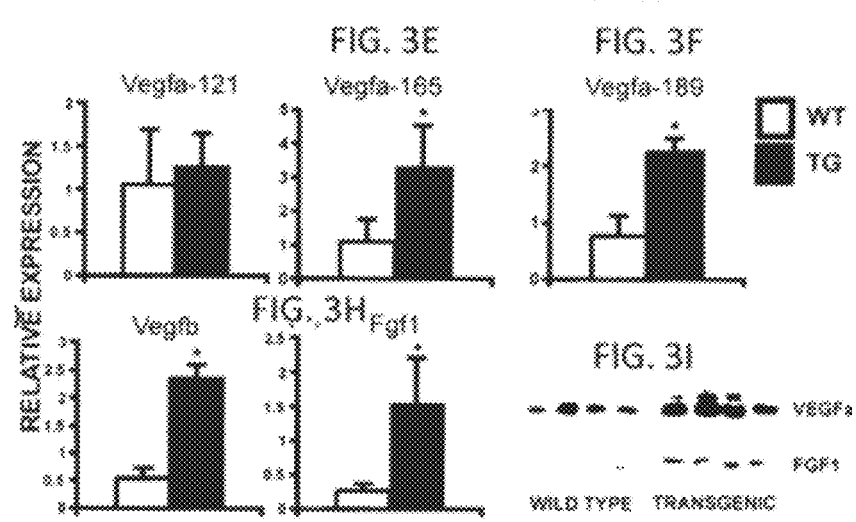

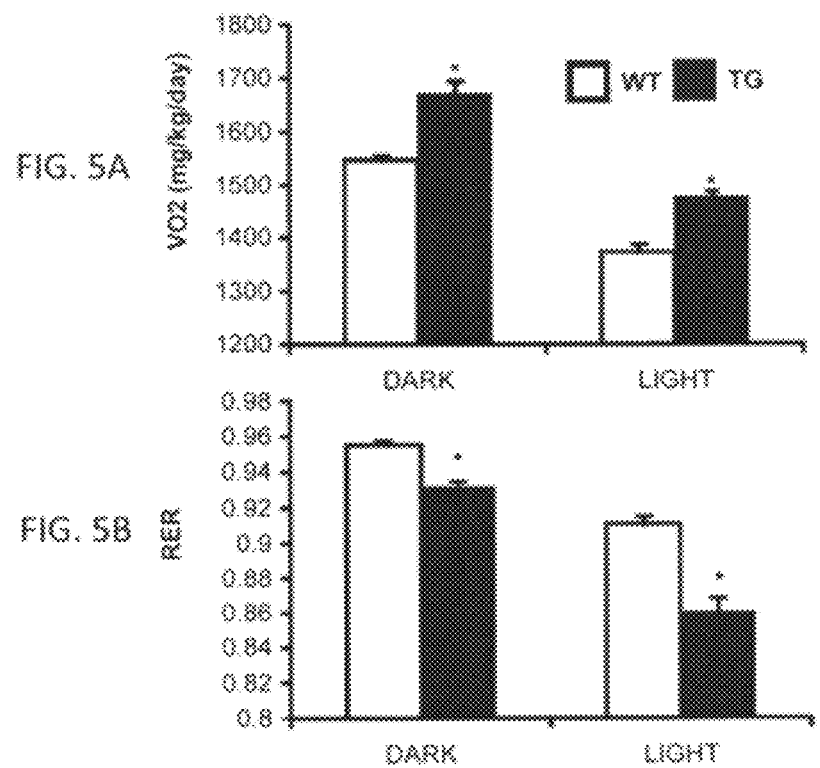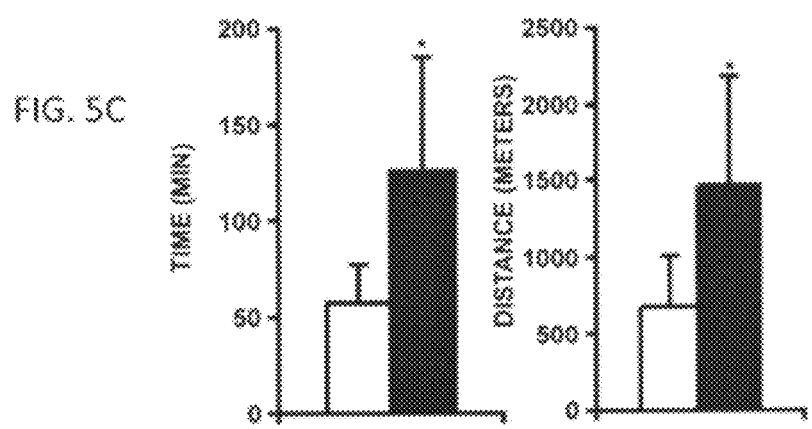

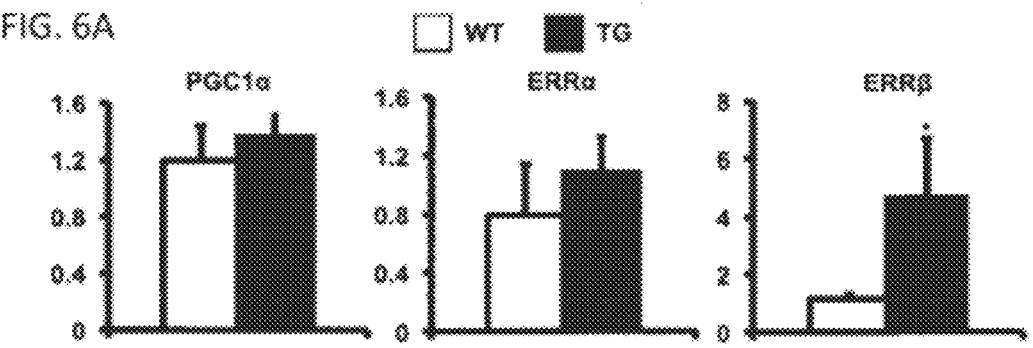
FIG. 6A
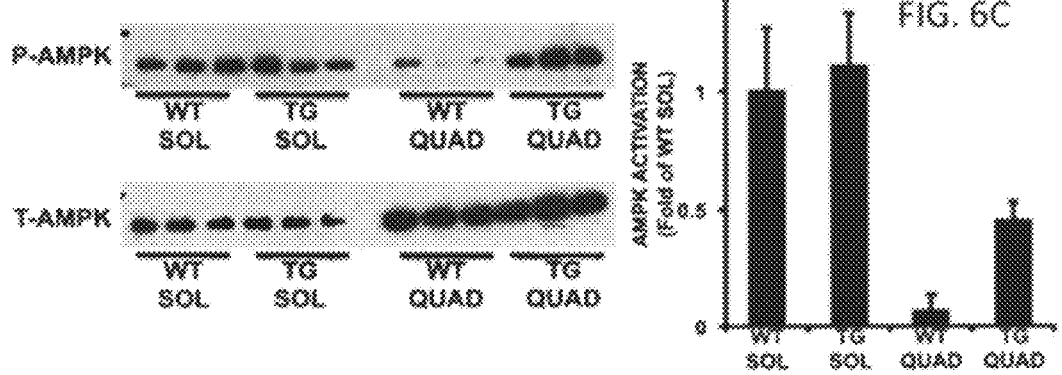
FIG. 6B
FIG. 6C
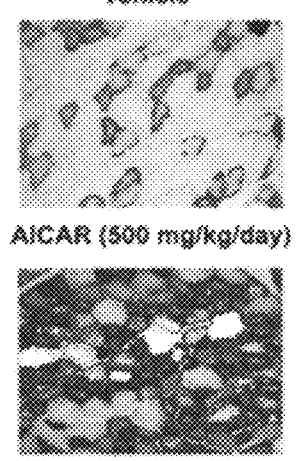
FIG. 6D
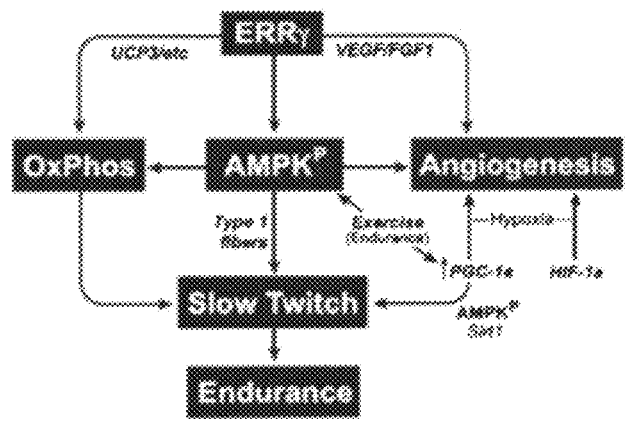
FIG. 6E

SEQUENCE LISTING

```
<160> NUMBER OF SEQ ID NOS: 2

<210> SEQ ID NO 1
<211> LENGTH: 3245
<212> TYPE: DNA
<213> ORGANISM: Homo sapiens
<220> FEATURE:
<221> NAME/KEY: CDS
<222> LOCATION: (488)..(1795)

<400> SEQUENCE: 1
tatccacaca cagcatcgga atattgctag ctaactcaac aaatgtgcaa atcaggggac      60
tgttgtgtgt gtaccgattc atgtctagac tgtttttatt ggtgaagtag gaactgcctc     120
atcagtcatg ggatcatagt gtcacagatg gaaaagcaac tatattagtc taaatatttg     180
attctgcagt tgcatgcacc aaattcagtg aggttagatg ttaaatcatc ttgttggctt     240
tgggctgaat ttgatctaag agacaaaagt ctcaaacaac agactactta ctgccaccac     300
atctcgattc aaagaatagt tttcacatgt tcgtggtgtg gaaaggactt tctgtttctc     360
actaatttct tcagctatac caagagtggt gttgtctttg aacaggaagg acagcaaaaa     420
taaacataac agttttttca taagatacac agctgcatta cacatcccaa aattgcttct     480 ctgcaga atg tca aac aaa gat cga cac att gat tcc agc tgt tcg tcc      529
        Met Ser Asn Lys Asp Arg His Ile Asp Ser Ser Cys Ser Ser
        1               5                   10 ttc atc aag acg gaa cct tcc agc cca gcc tcc ctg acg gac agc gtc      577
Phe Ile Lys Thr Glu Pro Ser Ser Pro Ala Ser Leu Thr Asp Ser Val
15                  20                  25                  30 aac cac cac agc cct ggt ggc tct tca gac gcc agt ggg agc tac agt      625
Asn His His Ser Pro Gly Gly Ser Ser Asp Ala Ser Gly Ser Tyr Ser
                35                  40                  45 tca acc atg aat ggc cat cag aac gga ctt gac tcg cca cct ctc tac      673
Ser Thr Met Asn Gly His Gln Asn Gly Leu Asp Ser Pro Pro Leu Tyr
            50                  55                  60 cct tct gct cct atc ctg gga ggt agt ggg cct gtc agg aaa ctg tat      721
Pro Ser Ala Pro Ile Leu Gly Gly Ser Gly Pro Val Arg Lys Leu Tyr
        65                  70                  75 gat gac tgc tcc agc acc att gtt gaa gat ccc cag acc aag tgt gaa      769
Asp Asp Cys Ser Ser Thr Ile Val Glu Asp Pro Gln Thr Lys Cys Glu
    80                  85                  90 tac atg ctc aac tcg atg ccc aag aga ctg tgt tta gtg tgt ggt gac      817
Tyr Met Leu Asn Ser Met Pro Lys Arg Leu Cys Leu Val Cys Gly Asp
```

```
                -continued
  95                100               105                110
atc gct tct ggg tac cac tat ggg gta gca tca tgt gaa gcc tgc aag      865
Ile Ala Ser Gly Tyr His Tyr Gly Val Ala Ser Cys Glu Ala Cys Lys
            115                 120                 125 gca ttc ttc aag agg aca att caa ggc aat ata gaa tac agc tgc cct      913
Ala Phe Phe Lys Arg Thr Ile Gln Gly Asn Ile Glu Tyr Ser Cys Pro
            130                 135                 140 gcc acg aat gaa tgt gaa atc aca aag cgc aga cgt aaa tcc tgc cag      961
Ala Thr Asn Glu Cys Glu Ile Thr Lys Arg Arg Arg Lys Ser Cys Gln
            145                 150                 155 gct tgc cgc ttc atg aag tgt tta aaa gtg ggc atg ctg aaa gaa ggg     1009
Ala Cys Arg Phe Met Lys Cys Leu Lys Val Gly Met Leu Lys Glu Gly
            160                 165                 170 gtg cgt ctt gac aga gta cgt gga ggt cgg cag aag tac aag cgc agg     1057
Val Arg Leu Asp Arg Val Arg Gly Gly Arg Gln Lys Tyr Lys Arg Arg
175                 180                 185                 190 ata gat gcg gag aac agc cca tac ctg aac cct cag ctg gtt cag cca     1105
Ile Asp Ala Glu Asn Ser Pro Tyr Leu Asn Pro Gln Leu Val Gln Pro
                195                 200                 205 gcc aaa aag cca tat aac aag att gtc tca cat ttg ttg gtg gct gaa     1153
Ala Lys Lys Pro Tyr Asn Lys Ile Val Ser His Leu Leu Val Ala Glu
            210                 215                 220 ccg gag aag atc tat gcc atg cct gac cct act gtc ccc gac agt gac     1201
Pro Glu Lys Ile Tyr Ala Met Pro Asp Pro Thr Val Pro Asp Ser Asp
            225                 230                 235 atc aaa gcc ctc act aca ctg tgt gac ttg gcc gac cga gag ttg gtg     1249
Ile Lys Ala Leu Thr Thr Leu Cys Asp Leu Ala Asp Arg Glu Leu Val
        240                 245                 250 gtt atc att gga tgg gcg aag cat att cca ggc ttc tcc acg ctg tcc     1297
Val Ile Ile Gly Trp Ala Lys His Ile Pro Gly Phe Ser Thr Leu Ser
255                 260                 265                 270 ctg gcg gac cag atg agc ctt ctg cag agt gct tgg atg gaa att ttg     1345
Leu Ala Asp Gln Met Ser Leu Leu Gln Ser Ala Trp Met Glu Ile Leu
                275                 280                 285 atc ctt ggt gtc gta tac cgg tct ctt tca ttt gag gat gaa ctt gtc     1393
Ile Leu Gly Val Val Tyr Arg Ser Leu Ser Phe Glu Asp Glu Leu Val
            290                 295                 300 tat gca gac gat tat ata atg gac gaa gac cag tcc aaa tta gca ggc     1441
Tyr Ala Asp Asp Tyr Ile Met Asp Glu Asp Gln Ser Lys Leu Ala Gly
            305                 310                 315 ctt ctt gat cta aat aat gct atc ctg cag ctg gta aag aaa tac aag     1489
Leu Leu Asp Leu Asn Asn Ala Ile Leu Gln Leu Val Lys Lys Tyr Lys
        320                 325                 330 agc atg aag ctg gaa aaa gaa gaa ttt gtc acc ctc aaa gct ata gct     1537
Ser Met Lys Leu Glu Lys Glu Glu Phe Val Thr Leu Lys Ala Ile Ala
335                 340                 345                 350 ctt gct aat tca gac tcc atg cac ata gaa gat gtt gaa gcc gtt cag     1585
Leu Ala Asn Ser Asp Ser Met His Ile Glu Asp Val Glu Ala Val Gln
                355                 360                 365 aag ctt cag gat gtc tta cat gaa gcg ctg cag gat tat gaa gct ggc     1633
Lys Leu Gln Asp Val Leu His Glu Ala Leu Gln Asp Tyr Glu Ala Gly
            370                 375                 380 cag cac atg gaa gac cct cgt cga gct ggc aag atg ctg atg aca ctg     1681
Gln His Met Glu Asp Pro Arg Arg Ala Gly Lys Met Leu Met Thr Leu
            385                 390                 395 cca ctc ctg agg cag acc tct acc aag gcc gtg cag cat ttc tac aac     1729
Pro Leu Leu Arg Gln Thr Ser Thr Lys Ala Val Gln His Phe Tyr Asn
400                 405                 410 atc aaa cta gaa ggc aaa gtc cca atg cac aaa ctt ttt ttg gaa atg     1777
```

```
Ile Lys Leu Glu Gly Lys Val Pro Met His Lys Leu Phe Leu Glu Met
415                 420                 425                 430 ttg gag gcc aag gtc tga ctaaaagctc cctgggcctt ccatccttc              1825
Leu Glu Ala Lys Val
            435 atgttgaaaa agggaaaata aacccaagag tgatgtcgaa gaaacttaga gtttagttaa    1885 caacatcaaa atcaacaga ctgcactgat aatttagcag caagactatg aagcagcttt    1945 cagattcctc cataggttcc tgatgagttc tttctacttt ctccatcatc ttctttcctc    2005 tttcttccca catttctctt tctctttatt ttttctcctt ttcttctttc acctccctta    2065 tttctttgct tctttcattc ctagttccca ttctcctttta ttttcttccc gtctgcctgc   2125 cttcttctt ttctttacct actctcattc ctctctttc tcatccttcc ccttttttct    2185 aaatttgaaa tagctttagt ttaaaaaaaa aaatcctccc ttccccctttt ccttcccttt   2245 tctttccttt ttccctttcc ttttcccttt ccttccttt cctcttgacc ttctttccat    2305 cttttctttt cttccttctg ctgctgaact tttaaaagag gtctctaact gaagagagat    2365 ggaagccagc cctgccaaag gatggagatc cataatatgg atgccagtga acttattgtg   2425 aaccataccg tccccaatga ctaaggaatc aaagagagag aaccaacgtt cctaaaagta   2485 cagtgcaaca tatacaaatt gactgagtgc agtattagat ttcatgggag cagcctctaa   2545 ttagacaact taagcaacgt tgcatcggct gcttcttatc attgcttttc catctagatc    2605 agttacagcc atttgattcc ttaattgttt tttcaagtct tccaggtatt tgttagttta   2665 gctactatgt aacttttttca gggaatagtt taagctttat tcattcatgc aatactaaag   2725 agaaataaga atactgcaat tttgtgctgg ctttgaacaa ttacgaacaa taatgaagga    2785 caaatgaatc ctgaaggaag atttttaaaa atgttttgtt tcttcttaca aatggagatt   2845 ttttttgtacc agctttacca ctttttcagcc atttattaat atgggaattt aacttactca   2905 agcaatagtt gaagggaagg tgcatatatt cacggatgca atttatgttg tgtgccagtc    2965 tggtcccaaa catcaatttc ttaacatgag ctccagtttta cctaaatgtt cactgacaca   3025 aaggatgaga ttacacctac agtgactctg agtagtcaca tatataagca ctgcacatga   3085 gatatagatc cgtagaattg tcaggagtgc acctctctac ttgggaggta caattgccat    3145 atgatttcta gctgccatgg tggttaggaa tgtgatactg cctgtttgca aagtcacaga    3205 ccttgcctca gaaggagctg tgagccagta ttcatttaag                          3245

<210> SEQ ID NO 2
<211> LENGTH: 435
<212> TYPE: PRT
<213> ORGANISM: Homo sapiens

<400> SEQUENCE: 2

Met Ser Asn Lys Asp Arg His Ile Asp Ser Ser Cys Ser Ser Phe Ile
1               5                   10                  15

Lys Thr Glu Pro Ser Ser Pro Ala Ser Leu Thr Asp Ser Val Asn His
            20                  25                  30

His Ser Pro Gly Gly Ser Ser Asp Ala Ser Gly Ser Tyr Ser Ser Thr
        35                  40                  45

Met Asn Gly His Gln Asn Gly Leu Asp Ser Pro Pro Leu Tyr Pro Ser
    50                  55                  60

Ala Pro Ile Leu Gly Gly Ser Gly Pro Val Arg Lys Leu Tyr Asp Asp
65                  70                  75                  80

Cys Ser Ser Thr Ile Val Glu Asp Pro Gln Thr Lys Cys Glu Tyr Met
```

```
                        85                  90                  95
Leu Asn Ser Met Pro Lys Arg Leu Cys Leu Val Cys Gly Asp Ile Ala
                100                 105                 110

Ser Gly Tyr His Tyr Gly Val Ala Ser Cys Glu Ala Cys Lys Ala Phe
            115                 120                 125

Phe Lys Arg Thr Ile Gln Gly Asn Ile Glu Tyr Ser Cys Pro Ala Thr
        130                 135                 140

Asn Glu Cys Glu Ile Thr Lys Arg Arg Lys Ser Cys Gln Ala Cys
145                 150                 155                 160

Arg Phe Met Lys Cys Leu Lys Val Gly Met Leu Lys Glu Gly Val Arg
                165                 170                 175

Leu Asp Arg Val Arg Gly Gly Arg Gln Lys Tyr Lys Arg Arg Ile Asp
            180                 185                 190

Ala Glu Asn Ser Pro Tyr Leu Asn Pro Gln Leu Val Gln Pro Ala Lys
        195                 200                 205

Lys Pro Tyr Asn Lys Ile Val Ser His Leu Leu Val Ala Glu Pro Glu
    210                 215                 220

Lys Ile Tyr Ala Met Pro Asp Pro Thr Val Pro Asp Ser Asp Ile Lys
225                 230                 235                 240

Ala Leu Thr Thr Leu Cys Asp Leu Ala Asp Arg Glu Leu Val Val Ile
                245                 250                 255

Ile Gly Trp Ala Lys His Ile Pro Gly Phe Ser Thr Leu Ser Leu Ala
            260                 265                 270

Asp Gln Met Ser Leu Leu Gln Ser Ala Trp Met Glu Ile Leu Ile Leu
        275                 280                 285

Gly Val Val Tyr Arg Ser Leu Ser Phe Glu Asp Glu Leu Val Tyr Ala
    290                 295                 300

Asp Asp Tyr Ile Met Asp Glu Asp Gln Ser Lys Leu Ala Gly Leu Leu
305                 310                 315                 320

Asp Leu Asn Asn Ala Ile Leu Gln Leu Val Lys Lys Tyr Lys Ser Met
                325                 330                 335

Lys Leu Glu Lys Glu Glu Phe Val Thr Leu Lys Ala Ile Ala Leu Ala
            340                 345                 350

Asn Ser Asp Ser Met His Ile Glu Asp Val Glu Ala Val Gln Lys Leu
        355                 360                 365

Gln Asp Val Leu His Glu Ala Leu Gln Asp Tyr Glu Ala Gly Gln His
    370                 375                 380

Met Glu Asp Pro Arg Arg Ala Gly Lys Met Leu Met Thr Leu Pro Leu
385                 390                 395                 400

Leu Arg Gln Thr Ser Thr Lys Ala Val Gln His Phe Tyr Asn Ile Lys
                405                 410                 415

Leu Glu Gly Lys Val Pro Met His Lys Leu Phe Leu Glu Met Leu Glu
            420                 425                 430

Ala Lys Val
        435
```

MODULATION OF ESTROGEN RECEPTOR-RELATED RECEPTOR GAMMA (ERRγ) AND USES THEREFOR

CROSS REFERENCE TO RELATED APPLICATION

This application claims priority to U.S. Provisional Application No. 61/447,704 filed Mar. 1, 2011, herein incorporated by reference.

ACKNOWLEDGMENT OF GOVERNMENT SUPPORT

This invention was made with government support under AR053803-03 awarded by the National Institute of Arthritis and Musculoskeletal and Skin Diseases; under HD027183 and DK057978 awarded by the National Institutes of Health, Department of Health and Human Services; and under U19DK62434-01 awarded by the Nuclear Receptor Signaling Atlas. The government has certain rights in the invention.

FIELD

This application relates to methods of increasing vascularization, muscle performance, and/or mitochondrial activity in subjects in need thereof, by administering a therapeutically effective amount of one or more agents that increases ERRγ activity to the subject. In some examples the subject does not receive additional exercise, and as such, the subject may be sedentary (such as bedridden or in a wheelchair).

BACKGROUND

Tissue vascular supply is tightly coupled to its oxidative capacity. This is especially evident in skeletal muscle beds, each enriched in either oxidative slow-twitch or glycolytic fast-twitch myofibers (Fluck and Hoppeler, 2003; Pette and Staron, 2000). Slow-twitch muscles are characterized by high mitochondrial content, fatigue resistant (type I) fibers and dense vascularity to ensure a steady and prolonged supply of oxygen and nutrients (Annex et al., 1998; Cherwek et al., 2000; Ripoll et al., 1979). Fast-twitch (type II) muscles generally have lower oxidative capacity, a reduced blood supply and are fatigue sensitive. How the type I vs. the type II muscle vasculature is specified to match oxidative capacity is unclear.

Previous studies established that nuclear receptors such as PPARα, PPARδ and ERRα along with co-regulators PGCα1α, PGC1β and Rip140 control diverse aspects of aerobic respiration including fatty acid oxidation, oxidative phosphorylation and mitochondrial biogenesis in skeletal muscle (Arany et al., 2007; Huss et al., 2004; Lin et al., 2002; Minnich et al., 2001; Muoio et al., 2002; Seth et al., 2007; Wang et al., 2004). While signaling factors such as TGFβ1, platelet-derived growth factor, fibroblast growth factor (FGF) 1 and 2, and vascular endothelial growth factor (VEGF) are known to stimulate angiogenesis (Carmeliet, 2000; Ferrara and Kerbel, 2005; Gustafsson and Kraus, 2001), whether and how these factors orchestrate dense vascularization of aerobic muscles is unclear. One possibility is vascular arborization by co-activator PGC1 α that is induced by hypoxia and exercise (Arany et al., 2008). However, PGC1α knockout mice are viable, still retain oxidative muscle, and have normal vasculature (Arany et al., 2008; (Lin et al., 2004). Since the intrinsic enrichment of blood flow to aerobic muscles in the absence of exercise is unlikely to depend on PGC1α induction, we speculate the existence of a novel regulatory angiogenic pathway.

Estrogen receptor-related receptor γ (ERRγ), like other members of the ERR subfamily, is a constitutively active orphan nuclear receptor, though unlike ERRα and β, it is more selectively expressed in metabolically active and highly vascularized tissues such as heart, kidney, brain and skeletal muscles (Giguere, 2008; Heard et al., 2000; Hong et al., 1999). In vitro data indicate that ERRγ activates genes such as PDK4 and MCAD that play a regulatory role in oxidative fat metabolism (Huss et al., 2002; Zhang et al., 2006). Furthermore, a comprehensive gene expression analysis identified ERRγ as a key regulator of multiple genes linked to both fatty acid oxidation and mitochondrial biogenesis in cardiac muscles (Alaynick et al., 2007; Dufour et al., 2007). Expression of ERRγ is also induced in variety of tumors with hypermetabolic demands and abundant vasculature (Ariazi et al., 2002; Cheung et al., 2005; Gao et al., 2006).

SUMMARY

The ability of ERRγ in controlling the intrinsic angiogenic pathway in oxidative slow-twitch muscles is demonstrated herein. It is shown herein that ERRγ is exclusively and abundantly expressed in oxidative (type I) slow-twitch muscles. Transgenic expression of ERRγ in fast-twitch type II muscle triggered aerobic transformation, mitochondrial biogenesis, VEGF induction and robust myofibrillar vascularization, all in the absence of exercise. It was observed that these intrinsic effects of ERRγ do not depend on PGC1 α induction, but rather are linked to activation of the metabolic sensor AMPK. These results reveal an exercise-independent ERRγ pathway that promotes and coordinates vascular supply and metabolic demand in oxidative slow-twitch muscles.

Based on these observations, provided herein are methods for increasing vascularization in a subject. For example, such methods can include administering a therapeutically effective amount of one or more agents that increases ERRγ activity to a mammal needing increased vascularization, such as vascularization in the mammal's muscle (such as skeletal or cardiac muscle), brain, kidney, or brown adipose tissue. In some examples, the method can also include selecting a mammal in need of increased vascularization or a mammal at risk for developing a disorder that can benefit from increased vascularization.

Methods for muscle rehabilitation (such as increasing or enhancing muscle performance) in a subject are provided. For example, such methods can include administering a therapeutically effective amount of one or more agents that increases ERRγ activity to a mammal needing muscle rehabilitation (such as increased or enhanced muscle performance), such as a subject having or at risk for muscle wasting. In some examples, the method can also include selecting a mammal in need of muscle rehabilitation (such as increased muscle performance) or a mammal at risk for developing a disorder that can benefit from muscle rehabilitation (such as increased muscle performance).

In addition, provided herein are methods for increasing mitochondrial activity in a subject. For example, such methods can include administering a therapeutically effective amount of one or more agents that increases ERRγ activity to a mammal needing increased mitochondrial activity. In some examples, the method can also include selecting a mammal in need of increased mitochondrial activity or a mammal at risk for developing a disorder that can benefit from increased mitochondrial activity.

In some examples, the methods do not include exercising the mammal. As such, in some examples the subject is one who cannot exercise or is sedentary, such as a person who is bedridden or confined to a wheelchair.

The foregoing and other objects and features of the disclosure will become more apparent from the following detailed description, which proceeds with reference to the accompanying figures.

BRIEF DESCRIPTION OF THE DRAWINGS

FIGS. 1A-F show skeletal muscle ERRγ expression. (A) ERRγ gene (lower panel) and/or protein (upper panel) expression in quadriceps (QUADS), white gastrocnemius (WG), red gastrocnemius (RG) and soleus (SOL) isolated from C57B1/6J mice (N=4). (B) Representative images of β-galactosidase stained muscles. (C) Expression of transgene transcript (lower panel) and protein (upper panel) in quadriceps of wild type (WT), founder TG 425 and 421. (D) Representative hindlimbs from WT and transgenic mice. (E) Dissected hindlimb muscle beds [adductor (ADDT), quadriceps, gastrocnemius (GASTROC) and soleus]. (F) Oxidative biomarker expression in wild type and transgenic mice. Protein expression levels of myoglobin and cytochrome c (cycs) in wild type, TG 425 and TG 421 quadriceps (N=3) are shown. In (A) and (C) data are presented as mean±SD (N=4). See FIG. 1F.

FIGS. 2A-E show that ERRγ promotes oxidative muscle transformation. (A) Gene ontology classification of positively regulated genes. Gene selection was based on p<0.05 on Bonferroni's multiple comparison test for fold change (N=3). (B) ERRγ increases expression of oxidative metabolism (Ucp3, Pdk4, Cycs, Cox5a, Lpl), oxidative muscle (Mhc1a, Mhc2a) but not glycolytic muscle (Mhc2b) biomarker genes. Data are presented as mean±SD from N=6 samples. (C) ERRγ increases protein expression of myoglobin, cytochrome c and uncoupling protein 3 (N=3). (D) Representative images of SDH stained WT and transgenic gastrocnemius cryo-sections. Similar results were obtained from N=4 mice. (E) OCAR/ECAR ratio representing a shift in cellular energy production to oxidative phosphorylation. Data is presented as mean±SD. * represents statistically significant difference between WT and transgenic mice or between WT and ERRγ over-expressing C2C12 cells (p<0.05, unpaired Student's t-test).

FIGS. 2F-G show ERRγ in cultured muscle cells. (F) ERRγ knockdown in primary myoblast. Primary myoblast were prepared from soleus and red gastrocnemius and infected with either control or ERRγ siRNA. Expression of ERRγ and oxidative biomarkers (cycs, ucp3, Acscll, Cox6a2, Ppara) was measured in control (open bars) and ERRγ (closed bars) knockdown primary muscle cells. Data is presented as mean±SD. (*) Indicates statistically significant difference between control and ERRγ knockdown cells (p<0.05, unpaired Student's t-test). (G-H) Mitochondrial bioenergetics in wild type and ERRγ over-expressing C2C12 cells. (G) Basal oxygen consumption rate (OCR) representing mitochondrial respiration. (H) Basal extracellular acidification rate (ECAR) representing glycolysis. Data are presented as mean±SD. (*) Indicates statistically significant difference between the two groups. (p<0.05, unpaired Student's t-test).

FIGS. 3A-I show that ERRγ increases muscle vascularization. (A) Increased PECAM 1 staining in transgenic compared to WT gastrocnemius. (B) Increased alkaline phosphatase staining in transgenic compared to WT tibialis muscles. (C) Confocal images of microsphere perfused WT and transgenic quadriceps. Similar results were obtained from N=4 experiments in (A-C). (D-H) Expression of Vegfa-121, Vegfa-165, Vegfa-189, Vegfb and Fgf1 transcript levels in WT and transgenic quadriceps. Data are presented as mean±SD from N=6 samples. (I) ERRγ increases VEGFa and FGF1 protein expression (N=4). * represents significant difference between WT and transgenic mice (p<0.05, unpaired Student's t-test).

FIGS. 5A-E show the physiological effect of ERRγ over-expression. (A) Average oxygen consumption (N=6-7) and (B) average RER (N=6-7) during the light and the dark cycle over a period of 24 hr in WT and transgenic mice. (C) Running endurance as a function of time and distance (N=6). (D) The ambulatory activity, measured using CLMAC units, is comparable between the wild type and the transgenic mice. (E) Average weight gain in wild type and transgenic mice on high fat diet (N=6). Data are presented as mean±SEM in (A), (B), and (D) and as mean±SD in (C) and (E). (*) Indicates statistically significant difference between the two groups. (p<0.05, unpaired Student's t-test).

FIGS. 6A-H show PGC1α-independent regulation by ERRγ. (A) Relative expression of Pgc1a, Erra and Errb genes in WT and transgenic muscle (N=6). Data are presented as mean±SD. * represents significant difference between WT and transgenic mice (p<0.05, unpaired Student's t-test). (B) Phospho (upper panel) and total (lower panel) AMPK in soleus (SOL) and quadriceps (QUAD) of WT and transgenic mice (N=3). (C) Quantification of AMPK activation (phospho to total AMPK ratio) by densitometric analysis, presented as fold of WT soleus (N=3). Data is presented as mean±SD. (D) Representative images of SDH staining of muscle cryo-sections from vehicle and AICAR (500 mg/kg/day for 4 weeks) treated mice. Similar results were obtained from N=3 mice. (E) Synchronization of metabolism and vasculature by ERRγ in aerobic muscle. (F) PGC1 a acetylation in the skeletal muscle. Nuclear extracts were prepared from freshly isolated quadriceps from wild type and ERRGO mice using a commercially available kit according to the manufacturer's instructions (Thermo Scientific* NE-PER* Nuclear and Cytoplasmic Extraction Kit, Cat no. P1-78833). PGC1 it was immunoprecipitated using anti-PGC1a antibody (Santacruz, Cat no. sc-13067) from the nuclear extracts and acetylation levels detected using anti-acetyl lysine antibody (Cell Signaling, Cat no. 9441S). Upper panel. Representative blots of acetylated and total PGC1a immunoprecipitated from wild type and ERRGO nuclear extracts. Lower panel. Densitometric analysis (using Image J) presented as the ratio of acetylated to total PGC1a in the wild type and ERRGO muscles. There is no statistically significant difference between the two groups. (G) Phospho-ACC levels in wild type and ERRγ transgenic muscle. ACC phosphorylation was measured in murine quadriceps using an antibody that specifically detects phospho-ACC (Cell Signaling, Cat no. 3661). The blot represents phospho-ACC levels in wild type and ERRγ transgenic quadriceps from N=3 samples in each group. (H) ATP levels in wild type and ERRγ over-expressing C2C12 cells. Absolute ATP level in C2C12 cells was measured using the ATP Bioluminescent Assay Kit according to manufacturer's instruction (Sigma, Cat No. FLAA-1KT). Briefly, $5 \times 10^4$ cells were lysed with 100 µl ATP releasing reagent for 10 minutes and combined with 100 µl water. The standards (20, 10, 2, 1, 0.2, and 0.1 µM) were made by mixing 100 µl ATP releasing reagent with 100 µl ATP solutions. Next, 100 µl ATP assay solution was added to a 96-well black plate with solid bottom and mixed with 100 µl samples or standards. Luminescence was measured using the EnVision plate reader (Perkin Elmer) and absolute ATP levels were calculated. ATP levels in wild type and ERR,/over-expressing 02012 cells are presented as mean±SD (nmol per 2×104 cells). * Represents statistically significant difference between groups (p<0.05, unpaired Student's t-test).

SEQUENCE LISTING

Figure 1A:

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. In the accompanying sequence listing:

SEQ ID NOS: 1 and 2 are the nucleic acid and corresponding amino acid sequence of an exemplary ERRγ sequence.

DETAILED DESCRIPTION

Unless otherwise explained, all technical and scientific terms used herein have the same meaning as commonly understood by one of ordinary skill in the art to which a disclosed invention belongs. The singular terms "a," "an," and "the" include plural referents unless context clearly indicates otherwise. Similarly, the word "or" is intended to include "and" unless the context clearly indicates otherwise. "Comprising" means "including." Hence "comprising A or B" means "including A" or "including B" or "including A and B."

Suitable methods and materials for the practice and/or testing of embodiments of the disclosure are described below. Such methods and materials are illustrative only and are not intended to be limiting. Other methods and materials similar or equivalent to those described herein can be used. For example, conventional methods well known in the art to which the disclosure pertains are described in various general and more specific references, including, for example, Benjamin Lewin, Genes V, published by Oxford University Press, 1994 (ISBN 0-19-854287-9); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8).

All publications, patent applications, patents, and other references mentioned herein are incorporated by reference in their entirety for all purposes. All sequences associated with the GenBank® Accession numbers mentioned herein are incorporated by reference in their entirety as were present on Mar. 1, 2012. Although exemplary GenBank® numbers are listed herein, the disclosure is not limited to the use of these sequences. Many other ERRγ sequences are publicly available, and can thus be readily used in the disclosed methods. In one example, an ERRγ sequence has at least 70%, at least 75%, at least 80%, at least 85%, at least 90%, at least 95%, at least 98%, or at least 100% sequence identity to any of the GenBank®numbers are listed herein.

In order to facilitate review of the various embodiments of the disclosure, the following explanations of specific terms are provided:

Administration: The introduction of a composition, such as an ERRγ agonist, into a subject by a chosen route, for example topically, orally, intravascularly such as intravenously, intramuscularly, intraperitoneally, intranasally, intradermally, transdermally, intrathecally, subcutaneously, via inhalation or via suppository. Administration can be local or systemic, such as intravenous or intramuscular. For example, if the chosen route is intravenous, the composition is administered by introducing the composition into a vein of the subject. In some examples an ERRγ agonist is administered to a subject at an effective dose.

Estrogen receptor-related receptor γ (ERRγ): (OMIM 602969) A constitutively active orphan nuclear receptor of the ERR subfamily. Unlike ERRα and β, it is more selectively expressed in metabolically active and highly vascularized tissues such as heart, kidney, brain and skeletal muscles.

ERRγ sequences are publicly available. For example, GenBank® Accession Nos. NM_001 134285.1, AY388461, AF058291.1 and NM_01 1935.2 disclose ERRγ nucleic acids, and GenBank® Accession Nos. NP_001127757.1, P62508.1, AAQ93381.1, and NP_036065.1 disclose ERRγ proteins. In certain examples, ERRγ has at least 80% sequence identity, for example at least 85%, 90%, 95%, or 98% sequence identity to such sequences (such as SEQ ID NO: 1 or 2), and retains ERRγ activity.

ERRγ activity includes the ability to promote vascularization (for example in skeletal muscle), increase mitochondrial activity (such as mitochondrial respiration), promote transformation of fast- to slow-twitch type muscle, promote muscle rehabilitation, and/or enhance muscle performance.

Isolated: An "isolated" biological component (such as a nucleic acid, protein or antibody) has been substantially separated, produced apart from, or purified away from other biological components in the cell of the organism in which the component naturally occurs, such as, other chromosomal and extrachromosomal DNA and RNA, and proteins. Nucleic acids and proteins which have been "isolated" thus include nucleic acids and proteins purified by standard purification methods. The term also embraces nucleic acids and proteins prepared by recombinant expression in a host cell as well as those chemically synthesized.

Pharmaceutically acceptable carriers: The pharmaceutically acceptable carriers useful in this disclosure are conventional. *Remington's Pharmaceutical Sciences*, by E. W. Martin, Mack Publishing Co., Easton, Pa., 15th Edition (1975), describes compositions and formulations suitable for pharmaceutical delivery of an ERRγ agonist or other agent that increases ERRγ activity.

In general, the nature of the carrier will depend on the particular mode of administration being employed. For instance, parenteral formulations usually include injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Recombinant: A recombinant nucleic acid molecule or protein is one that has a sequence that is not naturally occurring or has a sequence that is made by an artificial combination of two otherwise separated segments of sequence. This artificial combination can be accomplished by methods known in the art, such as chemical synthesis or by the artificial manipulation of isolated segments of nucleic acids, e.g., by genetic engineering techniques. Cells that express such molecules are referred to as recombinant or transgenic cells.

Sequence identity: The similarity between amino acid or nucleic acid sequences are expressed in terms of the similarity between the sequences, otherwise referred to as sequence identity. Sequence identity is frequently measured in terms of percentage identity (or similarity or homology); the higher the percentage, the more similar the two sequences are.

Methods of alignment of sequences for comparison are well known in the art. Various programs and alignment algorithms are described in: Smith and Waterman, *Adv. Appl. Math.* 2:482, 1981; Needleman and Wunsch, *J. Mal. Biol.* 48:443, 1970; Pearson and Lipman, *Proc. Natl. Acad. Sci. U.S.A.* 85:2444, 1988; Higgins and Sharp, *Gene* 73:237, 1988; Higgins and Sharp, *CABIOS* 5:151, 1989; Corpet et al., *Nucleic Acids Research* 16:10881, 1988; and Pearson and Lipman, *Proc. Natl. Acad. Sci. U.S.A.* 85:2444, 1988. Altschul et al., *Nature Genet.* 6:119, 1994, presents a detailed consideration of sequence alignment methods and homology calculations.

The NCBI Basic Local Alignment Search Tool (BLAST) (Altschul et al., *J. Mol. Biol.* 215:403, 1990) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet.

Variants of ERRγ that retain ERRγ activity are encompassed by this disclosure typically characterized by possession of at least about 75%, for example at least about 80%, at least 85%, at least 90%, at least 91%, at least 92%, at least 93%, at least 94%, at least 95%, at least 96%, at least 97%, at least 98% or at least 99% sequence identity counted over the full length alignment with the amino acid or nucleic acid sequence of interest, such as any of SEQ ID NOS: 1-2. Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

Subject: Living multi-cellular vertebrate organisms, a category that includes human and non-human mammals.

Therapeutically effective amount: An amount of a pharmaceutical preparation that alone, or together with a pharmaceutically acceptable carrier or one or more additional therapeutic agents, induces the desired response. A therapeutic agent, such as an ERRγ agonist, is administered in therapeutically effective amounts. In some embodiments, a therapeutically effective amount is the amount of one or more agents that increase ERRγ activity necessary to increase or more of vascularization (for example in skeletal muscle), mitochondrial activity (such as mitochondrial respiration), transformation of fast- to slow-twitch type muscle, and/or muscle performance (such as an increase of at least 20%, at least 50%, at least 60%, at least 75%, at least 80%, or at least 95% as compared to an absence of the ne or more agents that increase ERRγ activity). When administered to a subject, a dosage will generally be used that will achieve target tissue concentrations that has been shown to achieve a desired in vitro effect.

Effective amounts a therapeutic agent can be determined in many different ways, such as assaying for an increase in vascularization, mitochondrial activity transformation of fast- to slow-twitch type muscle, and/or muscle performance or improvement of physiological condition of a subject having or at risk for a disease such as a mitochondrial disease, vascular disease (such as cardiovascular disease, peripheral vascular disease, ischemia), or muscular disease (such as atrophy or sarcopenia). Effective amounts also can be determined through various in vitro, in vivo or in situ assays.

Therapeutic agents can be administered in a single dose, or in several doses, for example daily; during a course of treatment. However, the effective amount of can be dependent on the source applied, the subject being treated, the severity and type of the condition being treated, and the manner of administration.

Treating a disease: "Treatment" refers to a therapeutic intervention that ameliorates a sign or symptom of a disease or pathological condition after it has begun to develop, such a sign or symptom of a mitochondrial disease, vascular disease (such as cardiovascular disease, peripheral vascular disease, ischemia), or muscular disease (such as atrophy or sarcopenia). Treatment can also induce remission or cure of a condition, such as an ischemic stroke, transient ischemia attacks (TIAs), muscle atrophy, sarcopenia, MELAS, and hearing loss. Preventing a disease refers to a therapeutic intervention to a subject who does not exhibit signs of a disease or exhibits only early signs for the purpose of decreasing the risk of developing pathology, such that the therapy inhibits or delays the full development of a disease, such as preventing development of a mitochondrial disease, vascular disease (such as cardiovascular disease, peripheral vascular disease, ischemia), or muscular disease (such as atrophy or sarcopenia). Treatment and prevention of a disease does not require a total absence of disease. For example, a decrease of at least 20% or at least 50% can be sufficient. The beneficial effect can be evidenced, for example, by a delayed onset of clinical symptoms of the disease in a susceptible subject, a reduction in severity of some or all clinical symptoms of the disease, a slower progression of the disease, a reduction in the viral load, an improvement in the overall health or well-being of the subject, or by other parameters well known in'the art that are specific to the particular disease.

Upregulated or activation: When used in reference to the expression of a nucleic acid molecule, such as an ERRγ gene, refers to any process which results in an increase in production of a gene product. A gene product can be RNA (such as mRNA, rRNA, tRNA, and structural RNA) or protein (such as an ERRγ protein). Therefore, gene upregulation or activation includes processes that increase transcription of a gene or translation of mRNA.

Examples of processes that increase transcription include those that facilitate formation of a transcription initiation complex, those that increase transcription initiation rate, those that increase transcription elongation rate, those that increase processivity of transcription and those that relieve transcriptional repression (for example by blocking the binding of a transcriptional repressor). Gene upregulation can include inhibition of repression as well as stimulation of expression above an existing level. Examples of processes that increase translation include those that increase translational initiation, those that increase translational elongation and those that increase mRNA stability.

Gene upregulation includes any detectable increase in the production of a gene product. In certain examples, production of a gene product increases by at least 2-fold, for example at least 3-fold or at least 4-fold, as compared to a control (such an amount of gene expression in an untreated cell, such as a cell not contacted with an agent that increases ERRγ activity).

Vector: A nucleic acid molecule as introduced into a host cell, thereby producing a transformed host cell. A vector may include nucleic acid sequences that permit it to replicate in a host cell, such as an origin of replication. A vector may also include one or more selectable marker genes and other genetic elements known in the art.

Methods of Enhancing Vascularization, Muscle Rehabilitation, and Mitochondrial Activity It is shown herein that nuclear receptor ERRγ is highly expressed in type I skeletal muscle. Type I muscle is fatigue resistant, highly vascularized, aerobic, and slow-twitch. When ERRγ is transgenically expressed in anaerobic type II muscles (ERRGO mice), dually induces metabolic and vascular transformation in absence of exercise. ERRGO mice showed increased expression of genes promoting fat metabolism, mitochondrial respiration and type I fiber specification. Muscles in ERRGO mice also display an activated angiogenic program marked by myofibrillar induction and secretion of pro-angiogenic factors, neo-vascularization and a 100% increase in running endurance. At a functional level, these genetic changes impart high oxygen consuming and exercising capacity as well as resistance to diet-induced obesity to the ERRGO mice. Surprisingly, the induction of type I muscle properties by ERRγ does not involve PGC1α. Instead, ERRγ genetically activates the energy sensor AMPK, in mediating the metabo-vascular changes in the ERRGO mice. Therefore, ERRγ represents a previously unrecognized determinant that specifies intrinsic vascular and oxidative metabolic features that distinguish type I from type II muscle.

Although skeletal muscle adapts to exercise by increasing oxidative metabolism and vascular supply via induction of transcriptional regulators such as PGC1α (Arany et al., 2008; Baar et al., 2002; Huss et al., 2002; Pilegaard et al., 2003; Russell et al., 2003; Russell et al., 2005), how type I fibers achieve intrinsic vascularization even in absence of exercise is poorly understood. It is shown herein that one such molecular pathway involves nuclear receptor ERRγ, which is highly expressed in oxidative slow-twitch muscles. Targeted expression of ERRγ to quadriceps and white gastrocnemius, where the receptor is typically not expressed, morphologically endows these muscles with dense vascular supply and numerous slow-twitch characteristics.

Genome-wide expression analysis revealed that ERRγ acts by coordinately inducing gene networks promoting mitochondrial biogenesis, oxidative transformation and angiogeneis. The ERRγ program includes mobilization and oxidation of fat [e.g., Acadl, Acadm, Cpt1b, Cpt2, Lpl], electron transport [e.g., Atp5h, Cox6a2, Ndufab1, Ndufb2m Ndufv1, Sdhb], mitochondrial biogenesis [e.g., Mfn1], and formation of energy efficient slow-contractile muscle [e.g., Tnnc1, Tnni1, Tnnt1]. The observed changes constituting transformation of the contractile apparatus to a slow phenotype and increase in oxidative metabolic genes reflected in profound increase in mitochondrial (SDH) staining represents a fiber type switch. Notably, ERRγ also induces key transcriptional inducers of oxidative metabolism including Esrrb, Ppara, Ppard and Ppargc1b (Table 4) (Lin et al., 2002; Minnich et al., 2001; Muoio et al., 2002; Wang et al., 2004). Therefore, ERRγ may be an upstream genetic switch that determines metabolic fate by presiding over the expression of multiple aerobic regulators.

Without wishing to be bound by a particular model, it is proposed that the vascular program triggered by myocellular ERRγ activates a transcriptional program that directs secretion of paracrine signals into skeletal muscle microenvironment to induce angiogenesis. This model is strongly supported by the observation herein that conditioned media from ERRγ over-expressing C2C12 myotubules induces endothelial cell tube formation in culture. Indeed, ERRγ transcriptionally induced all isoforms of angiokine Vegfa in C2C12 myotubes, resulting in increased Vegfa secretion into the media. Vegfa is a key regulator of angiogenesis critical for guiding endothelial cells to their targets (Grunewald et al., 2006; Springer et al., 1998). Furthermore, ERRγ stimulates the Vegfa promoter containing putative ERR binding sites that is known to transcribe all Vegfa isoforms (Arany et al., 2008). Vegfa mRNA and protein expression is also induced in ERRGO muscle. These findings collectively indicate direct transcriptional activation of angiogenic genes by ERRγ. However, the angiogenic effects of ERRγ cannot be solely attributed to Vegfa induction and secretion. For example ERRγ additionally activates the expression of Fgf1 and Cxcl12, known to regulate endothelial cell proliferation and migration (Forough et al., 2006; Gupta et al., 1998; Partridge et al., 2000; Shao et al., 2008; Zheng et al., 2007), along with ephrin B2 proposed to recruit mural cells that are required for vessel maturation (Foo et al., 2006). Additionally, up-regulated factors such as Notch4 as well as SOX17 are transcriptional regulators of vasculogenesis (Hainaud et al., 2006; Leong et al., 2002; Matsui et al., 2006). In this aspect, ERRγ seems to serve a function similar to HIF1α, a regulator of angiogenesis during hypoxia (Pajusola et al., 2005). Interestingly, it was recently demonstrated that ERRs might physically interact with HIF1α in regulating its transcriptional activity (Ao et al., 2008). HIF1α mRNA levels—a marker for chronic hypoxia—did not change in ERRGO compared to wild type muscles indicating an absence of hypoxia or its involvement in the vascular effects of ERRγ (Hoppeler and Vogt, 2001a, b). Furthermore, HIF1α is known to negatively regulate oxidative metabolism (Mason et al., 2004; Mason et al., 2007) and is therefore unlikely to contribute to ERRγ-mediated remodeling of skeletal muscles.

ERRGO mice exhibited increased oxygen consumption, decreased respiratory exchange ratio, high running endurance and resistance to diet-induced weight gain. These changes are physiological hallmarks of increased aerobic capacity in mice, and are a direct consequence of engineering highly oxidative and vascularized muscle by ERRγ. While similar remodeling of skeletal muscle and aerobic physiology are triggered by exercise, the data herein demonstrate that generation of a fully functional "endurance vasculature" is not exercise dependent (Bloor, 2005; Egginton, 2008; Gavin et al., 2007; Gustafsson and Kraus, 2001; Jensen et al., 2004; Waters et al., 2004).

A surprising finding was lack of change in the expression of PGC1α, a known and inducible regulator of aerobic muscles, in the ERRγ-transformed muscle. One alternative possibility is post-translational activation of PGC1α without change in its expression (Jager et al., 2007; Puigserver et al., 2001; Rodgers et al., 2005). De-acetylation of PGC1α is critical for its activation in the skeletal muscle (Canto et al., 2010; Gerhart-Hines et al., 2007; Lagouge et al., 2006). However, ERRγ over-expression did not lead to de-acetylation of PGC1α, which remained comparably acetylated in both the wild type and ERRGO muscles. The lack of post-translational activation of the co-factor in ERRGO mice is further underscored by a previous report that non-genomic activation of PGC1α typically leads to its transcriptional induction, which we did not observe in these studies (Jäger et al., 2007). Along the same lines, it was recently shown that both PGC1α and β are dispensable for fiber type specification in the skeletal muscle (Zechner et al., 2010). In contrast, an alternative aerobic master regulator, AMPK, was found to be activated by ERRγ in the skeletal muscles. AMPK is typically activated by exercise (Fujii et al., 2000; Winder and Hardie, 1996; Wojtaszewski et al., 2000) and is essential for exercise-mediated switch to aerobic myofibers in the skeletal muscle (Rockl et al., 2007). Indeed, transgenic activation of AMPK in the skeletal muscle increases the proportions of oxidative myofibers in absence of any exercise (Rockl et al., 2007). It is shown herein that chemical activation of AMPK by AICAR triggers aerobic transformation of type II muscle. However, AMPK alone is unlikely to mediate all the ERRγ effects, and contribution by additional metabolic regulators (e.g., calcineurin, SIRT1, etc.) in ERRGO mice cannot be ruled out. This is possible because, unlike ERRγ, AMPK activation apparently does not lead to a complete transformation to a type I phenotype, but to a more intermediate type IIa and IIx oxidative myofibers (Rockl et al., 2007). In this context, it is peculiar that AMPK was naturally and selectively active in soleus (pre-dominantly type I myofibers) compared to quadriceps (pre-dominantly type II myofibers). Previous studies have suggested AMPK activity to be similar between soleus and EDL (also pre-dominantly made up of type II myofibers) (Dzamko et al., 2008; Jensen et al., 2007; Jorgensen et al., 2004). Speculatively, this discrepancy may have technical attributes or may even be linked to possible differences in recruitment of EDL and quadriceps for postural activity that might affect basal AMPK activation. Nevertheless, the results herein demonstrate that in the context of over-expression, ERRγ is sufficient to initiate both metabolic and vascular pathways to drive aerobic remodeling of sedentary muscle independent of PGC1α by recruiting alternative regulators such as AMPK (see FIG. 6E).

Multiple diseases including obesity and diabetes are commonly linked to deregulation of both oxidative metabolism and vascularity. A shared therapeutic approach to these conditions includes exercise that activates a plethora of transcriptional pathways to increase aerobic metabolism and vascularization to ultimately enhance performance (Bloor, 2005; Egginton, 2008; Gavin et al., 2007; Gustafsson and Kraus, 2001; Jensen et al., 2004; Waters et al., 2004). These findings indicate that regulation of ERRγ activity can be used to simultaneously regulate oxidative capacity and vascularity. High expression levels of this receptor in tissues most prone to metabolic and vascular diseases (e.g., heart, skeletal muscle, brain and kidney) further potentiates its value as a pharmacologic target (Ariazi et al., 2002; Cheung et al., 2005; Gao et al., 2006; Giguere, 2008; Heard et al., 2000; Hong et al., 1999). In summary, it is shown herein that ERRγ controls mitochondrial function and metabolism, together with angiogenesis that anatomically synchronizes vascular arborization to oxidative metabolism.

Based on this observation, provided herein are methods of increasing vascularization, mitochondrial activity, muscle rehabilitation and/or muscle endurance by increasing ERRγ activity, for example by use of ERRγ nucleic acids, proteins, agonists, or combinations thereof. Such methods can be used to treat or prevent a disorder associated with defects in vascularization or mitochondrial activity, as well as disorders that may result from being sedentary or being unable to exercise. The agent(s) which enhance ERRγ activity can be administered by any suitable means, including parenteral, subcutaneous, intraperitoneal, intrapulmonary, and intranasal. Parenteral infusions include intramuscular, intravenous, intracerebral, intraarterial, intraperitoneal, or subcutaneous administration. In some embodiments, the dosing is given by injections, such as intravenous or intramuscular injections, depending in part on whether the administration is brief or chronic.

In some examples, the methods do not include providing additional exercise to the subject being treated with the agents that increase ERRγ activity. For example, the subject may undergo some moderate activity during such treatment (such as that needed to perform menial tasks), the subject does not undergo any strenuous activity (such as running, biking, swimming, or walking for more than 5 or 10 minutes at a time). In some examples, the subject treated is one who cannot exercise, such as one confined to a bed or wheelchair. In another example, the subject treated is one who is sedentary, such as one with no or irregular physical activity, for example one who sits or remains inactive for most of the day with little or no exercise.

In one example, methods are provided for increasing vascularization. Such methods can include administering a therapeutically effective amount of one or more agents that increase ERRγ activity to a mammal needing increased vascularization. In some examples, the method increases vascularization in the desired tissue by at least 25%, at least 40%, at least 50%, at least 60%, at least 70%, at least 80%, at least 90%, or at least 100%, as compared to an amount of vascularization in the absence of administration of the one or more agents that increases ERRγ activity. Methods of measuring vascularization are provided herein and are known in the art, and can include measuring expression of one or more VEGF molecules, detection of vasculature (for example using angiography), and the like. In some examples, the method also includes selecting a mammal in need of increased vascularization or a mammal at risk for developing a disorder that can benefit from increased vascularization. In one example, vascularization is needed or occurs in the mammal's muscle, brain, kidney, or brown adipose tissue. Thus, the agents that increase ERRγ activity can be used for the prophylaxis or treatment of a mammal, for instance, a human subject who has been diagnosed with a vascular disorder, such as ischemia or peripheral vascular disease (PVD), or a person at risk for developing a vascular' disorder, such as one who is sedentary or is unable to exercise.

In some embodiments, the agents that increase ERRγ activity is administered to treat or prevent the development of a vascular disorder in skeletal muscle. For example, the subject may have or be at risk for muscle atrophy, sarcopenia, or peripheral vascular disease (such as peripheral arterial disease, PAD). In some embodiments, the agents that increase ERRγ activity is administered to treat or prevent the development of a vascular disorder in cardiac muscle. For example, the subject may have or be at risk for a heart attack or ischemia in a cardiac muscle. In some embodiments, the agents that increase ERRγ activity is administered to treat or prevent the development of a vascular disorder in the brain. For example, the subject may have or be at risk for a cerebrovascular disease, such as ischemic stroke, migraines, transient ischemic attacks (TIAs), dementia and the like. In some embodiments, the agents that increase ERRγ activity is administered to treat or prevent the development of a vascular disorder in the kidney. For example, the subject may have or be at risk for a kidney failure. In some embodiments, the agents that increase ERRγ activity is administered to treat or prevent the development of a vascular disorder in brown adipose tissue. For example, the subject may have or be at risk for obesity (such as diet-induced obesity). One skilled in the art will appreciate that complete elimination of symptoms associated with the vascular disorder is not required for the method to be effective, as long as at least some symptoms are eased.

In one example, methods are provided for increasing mitochondrial activity. Such methods can include administering a therapeutically effective amount of one or more agents that increase ERRγ activity to a mammal needing increased mitochondrial activity. In some examples, the method increases mitochondrial activity by at least 25%, at least 40%, at least 50%, at least 60%, at least 70%, at least 80%, at least 90%, or at least 100%, as compared to an amount of mitochondrial activity in the absence of administration of the one or more agents that increases ERRγ activity. Methods of measuring mitochondrial activity are provided herein and are known in the art, and can include measuring mitochondrial respiration, expression of mitochondrial genes, and the like. In some examples, the method also includes selecting a mammal in need of increased mitochondrial activity or a mammal at risk for developing a disorder that can benefit from increased mitochondrial activity. In one example, increased mitochondrial activity is needed or occurs in the mammal's muscle (e.g., skeletal or cardiac), brain, or ear. Thus, the agents that increase ERRγ activity can be used for the prophylaxis or treatment of a mammal, for instance, a human subject who has been diagnosed with a mitochondrial disorder, such as mitochondrial myopathy, encephalomyopathy, lactic acidosis, stroke-like symptoms (MELAS), or a person at risk for developing a mitochondrial disorder, such as one who is sedentary or is unable to exercise.

In some embodiments, the agents that increase ERRγ activity is administered to treat or prevent the development of a mitochondrial disorder in skeletal muscle. For example, the subject may have or be at risk for muscle atrophy, sarcopenia, or muscle wasting. In some embodiments, the agents that increase ERRγ activity is administered to treat or prevent the development of hearing loss, Leber's hereditary optic neuropathy (LHON), or mitochondrial encephalomyopathy, lactic acidosis, and stroke-like episode syndrome (MELAS). One skilled in the art will appreciate that complete elimination of symptoms associated with the mitochondrial disorder is not required for the method to be effective, as long as at least some symptoms are eased.

In one example, methods are provided for muscle rehabilitation (such as increasing muscle performance). Such methods can include administering a therapeutically effective amount of one or more agents that increase ERRγ activity to a mammal needing muscle rehabilitation (such as increased muscle performance). In some examples, the method increases muscle rehabilitation or performance by at least 25%, at least 40%, at least 50%, at least 60%, at least 70%, at least 80%, at least 90%, or at least 100%, as compared to an amount of muscle performance in the absence of administration of the one or more agents that increases ERRγ activity. In some examples, the method increases aerobic transformation of a type II muscle by at least 25%, at least 40%, at least 50%, at least 60%, at least 70%, at least 80%, at least 90%, or at least 100%, as compared to an amount of aerobic transformation of a type II muscle (e.g., quadriceps or white gastrocnemius) in the absence of administration of the one or more agents that increases ERRγ activity. In some examples, the method increases an amount of type I fibers in a muscle by at least 25%, at least 40%, at least 50%, at least 60%, at least 70%, at least 80%, at least 90%, or at least 100%, as compared to an amount of type I fibers in a muscle in the absence of administration of the one or more agents that increases ERRγ activity. Methods of measuring muscle performance are provided herein and are known in the art, and can include measuring the strength and endurance of the muscle, testing creatine kinase levels in the blood, electromyography (measuring electrical activity in muscles), elastography, and the like. In some examples, the method also includes selecting a mammal in need of muscle rehabilitation (such as increased muscle performance) or a mammal at risk for developing a disorder that can benefit from muscle rehabilitation (such as increased muscle performance). In one example, the muscle rehabilitated is skeletal muscle or cardiac muscle. Thus, the agents that increase ERRγ activity can be used for the prophylaxis or treatment of a mammal, for instance, a human subject who has been diagnosed with a muscle performance disorder, muscle atrophy or sarcopenia, or a person at risk for developing a muscle performance disorder, such as one who is sedentary or is unable to exercise.

Thus, increasing ERRγ activity, for example without the addition of exercise, can result in one or more of the following in skeletal or cardiac muscle: increased oxidative metabolism (such as one or more of aerobic transformation of fast-twitch muscles, increased mitochondrial biogenesis and respiration, increased lipid metabolism, increased fatigue-resistant type I fibers, increase running endurance), increased vascularization (such as one or more of increased synthesis and release of pro-angiogenic factors by myotubes, increased vascularization of skeletal muscle (e.g., hyper-vascularization). Thus, increasing ERRγ activity can enhance muscle performance, such as performance of type II muscles, such as quadriceps and white gastrocnemius. In one example, increasing ERRγ activity increases expression of or more of myoglobin, cytochrome c and UCP3, and has increased oxidative myofibers, relative to untreated muscle. In some examples such increases are an at least 1.5-fold or an at least 2-fold increase.

Increasing ERRγ Activity

The present disclosure provides methods and pharmaceutical compositions for increasing vascularization, mitochondrial activity, and/or muscle performance by increasing ERRγ activity and thereby treating or preventing disorders associated with decreased vascularization, muscle performance, or mitochondrial activity. ERRγ activity may be increased by increasing the amount of ERRγ protein being produced or by enhancing the activity of ERRγ protein. This can be achieved, for example, by administering a nucleotide sequence encoding for an ERRγ protein, an agent which enhances ERRγ expression, a substantially purified ERRγ protein, or an ERRγ agonist. An ERRγ agonist includes compounds which increase the ERRγ activity in a cell or tissue.

Administration of ERRγ Proteins

In one example, ERRγ activity is increased by administering to the subject an ERRγ protein, such as a pharmaceutical composition containing such a protein. ERRγ protein sequences are known. For example, GenBank® Accession Nos. NP_001127757.1, P62508.1, AAQ93381.1, and NP_036065.1 disclose exemplary ERRγ protein sequences. However, one skilled in the art will appreciate that variations of such proteins can also retain ERRγ activity. For example such variants may include one or more deletions, substitutions, or additions (or combinations thereof), such as 1-50 of such changes (such as 1-40, 1-30, 1-20, or 1-10 of such changes). In certain examples, ERRγ has at least 80%, at least 85%, at least 90%, at least 95%, at least 97%, at least 98% or at least 99% sequence identity to such sequences (such as SEQ ID NO: 2), and retains ERRγ activity. In some examples, changes are not made to the ERRγ ligand binding domain (LBD). In some examples, residues Asp328, Arg316 and/or Asp275 are not changed.

One of skill will realize that variants of ERRγ proteins can be used, such as a variant containing conservative amino acid substitutions. Such conservative variants will retain critical amino acid residues necessary for ERRγ activity, and will retain the charge characteristics of the residues in order to preserve the low pI and low toxicity of the molecules. Amino acid substitutions (such as at most one, at most two, at most three, at most four, at most five, or at most 10 amino acid substitutions, such as 1 to 10 or 1 to 5 conservative substitutions) can be made in an ERRγ protein sequence to increase yield. Conservative amino acid substitution tables providing functionally similar amino acids are well known to one of ordinary skill in the art. The following six groups are examples of amino acids that are considered to be conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

An ERRγ protein can be derivatized or linked to another molecule (such as another peptide or protein). For example, the ERRγ protein can be functionally linked (by chemical coupling, genetic fusion, noncovalent association or otherwise) to one or more other molecular entities, such as an antibody, a detection agent, or a pharmaceutical agent.

Methods of making proteins are routine in the art, for example by recombinant molecular biology methods or by chemical peptide synthesis. In one example, an ERRγ protein is expressed in a cell from a vector encoding the protein. In some examples, the expression vector encoding ERRγ also encodes a selectable marker. In some examples, the sequence encoding ERRγ also encodes a purification tag sequence (such as a His-tag, β-globin-tag or glutathione S-transferase-(GST) tag) at the N- or C-terminus of ERRγ, to assist in purification of the protein.

For example, expression of nucleic acids encoding ERRγ proteins can be achieved by operably linking the ERRγ DNA, or cDNA to a promoter (which is either constitutive or inducible), followed by incorporation into an expression cassette. The promoter can be any promoter, including a cytomegalovirus promoter and a human T cell lymphotrophic virus promoter (HTLV)-1. Optionally, an enhancer, such as a cytomegalovirus enhancer, is included in the construct. The cassettes can be suitable for replication and integration in either prokaryotes (such as *E. coli*) or eukaryotes (such as yeast or a mammalian cell). Typical expression cassettes contain specific sequences useful for regulation of the expression of the DNA encoding the protein. For example, the expression cassettes can include appropriate promoters, enhancers, transcription and translation terminators, initiation sequences, a start codon (i.e., ATG) in front of a protein-encoding gene, splicing signal for introns, sequences for the maintenance of the correct reading frame of that gene to permit proper translation of mRNA, and stop codons. The vector can encode a selectable marker, such as a marker encoding drug resistance (for example, ampicillin or tetracycline resistance).

To obtain high level expression of ERRγ, expression cassettes can include a strong promoter to direct transcription, a ribosome binding site for translational initiation (internal ribosomal binding sequences), and a transcription/translation terminator. Exemplary control sequences include the T7, trp, lac, tac, trc, or lambda promoters, the control region of fd coat protein, a ribosome binding site, and can include a transcription termination signal. For eukaryotic cells, the control sequences can include a promoter and/or an enhancer derived from, for example, an immunoglobulin gene, HTLV, SV40, polyoma, adenovirus, retrovirus, baculovirus, simian virus, promoters derived from the promoter for 3-phosphoglycerate kinase, the promoters of yeast acid phosphatase, the promoter of the yeast alpha-mating factors or cytomegalovirus, and a polyadenylation sequence, and can further include splice donor and/or acceptor sequences (for example, CMV and/or HTLV splice acceptor and donor sequences). The cassettes can be transferred into the chosen host cell by well-known methods such as transformation or electroporation for *E. coli* and calcium phosphate treatment, electroporation or lipofection for mammalian cells. Cells transformed by the cassettes can be selected by resistance to antibiotics conferred by genes contained in the cassettes, such as the amp, gpt, neo and hyg genes.

When the host is a eukaryote, such methods of transfection of DNA as calcium phosphate coprecipitates, conventional mechanical procedures such as microinjection, electroporation, insertion of a plasmid encased in liposomes, or virus vectors may be used. Eukaryotic cells can also be cotransformed with polynucleotide sequences encoding EERγ, and a second foreign DNA molecule encoding a selectable phenotype, such as the herpes simplex thymidine kinase gene. Another method is to use a eukaryotic viral vector, such as simian virus 40 (SV40), retrovirus, adenovirus, adeno-associated virus, Herpes virus, or bovine papilloma virus, to transiently infect or transform eukaryotic cells and express the protein (see for example, *Eukaryotic Viral Vectors*, Cold Spring Harbor Laboratory, Gluzman ed., 1982). One can readily use an expression system, such as plasmids and vectors, to produce proteins in cells including higher eukaryotic cells such as the COS, CHO, HeLa, fibroblast cell lines, lymphoblast cell lines, and myeloma cell lines.

Once expressed, the recombinant ERRγ protein can be purified according to standard procedures of the art, including ammonium sulfate precipitation, affinity columns, column chromatography, and the like (see, generally, R. Scopes, PROTEIN PURIFICATION, Springer-Verlag, N.Y., 1982). The recovered ERRγ protein need not be 100% pure. Once purified, partially or to homogeneity as desired, the ERRγ protein can be used therapeutically.

Modifications can be made to a nucleic acid encoding ERRγ without diminishing its biological activity. Some modifications can be made to facilitate the cloning, expression, or incorporation of ERRγ into a fusion protein. Such modifications are well known and include, for example, termination codons, a methionine added at the amino terminus to provide an initiation, site, additional amino acids placed on either terminus to create conveniently located restriction sites, or additional amino acids (such as poly His) to aid in purification steps.

In one example, ERRγ protein is synthesized by condensation of the amino and carboxyl termini of shorter fragments.

Methods of forming peptide bonds by activation of a carboxyl terminal end (such as by the use of the coupling reagent N,N'-dicylohexylcarbodimide) are well known.

Expression of ERRγ in a Subject

In one example, ERRγ activity is increased by administering to the subject a nucleic acid molecule encoding an ERRγ protein. ERRγ coding sequences are known. For example, GenBank® Accession Nos. NM_001134285.1, AY388461, AF058291.1 and NM_011935.2 disclose exemplary ERRγ nucleic acid sequences. However, one skilled in the art will appreciate that variations of such sequences can also encode a protein with ERRγ activity. For example such variants may include encode a protein with one or more deletions, substitutions, or additions (or combinations thereof), such as 1-50 of such changes (such as 1-40, 1-30, 1-20, or 1-10 of such changes). In certain examples, an ERRγ coding sequence has at least 80%, at least 85%, at least 90%, at least 95%, at least 97%, at least 98% or at least 99% sequence identity to such sequences (such as SEQ ID NO: 1), and encodes a protein having ERRγ activity. One of skill in the art can readily use the genetic code to construct a variety of functionally equivalent nucleic acids, such as nucleic acids which differ in sequence but which encode the same ERRγ protein sequence.

Nucleic acid sequences encoding a ERRγ protein can be prepared by any suitable method including, for example, cloning of appropriate sequences or by direct chemical synthesis by methods such as the phosphotriester method of Narang et al., *Meth. Enzymol.* 68:90-99, 1979; the phosphodiester method of Brown et al., *Meth. Enzymol.* 68:109-151, 1979; the diethylphosphoramidite method of Beaucage et al., *Tetra. Lett.* 22:1859-1862, 1981; the solid phase phosphoramidite triester method described by Beaucage & Caruthers, *Tetra. Letts.* 22(20):1859-1862, 1981, for example, using an automated synthesizer as described in, for example, Needham-VanDevanter et al., *Nucl. Acids Res.* 12:6159-6168, 1984; and, the solid support method of U.S. Pat. No. 4,458,066. Chemical synthesis produces a single stranded oligonucleotide. This can be converted into double stranded DNA by hybridization with a complementary sequence or by polymerization with a DNA polymerase using the single strand as a template. One of skill will recognize that longer sequences may be obtained by the ligation of shorter sequences.

Exemplary ERRγ nucleic acids can be prepared by routine cloning techniques. Examples of appropriate cloning and sequencing techniques, and instructions sufficient to direct persons of skill through many cloning exercises are found in Sambrook et al., supra, Berger and Kimmel (eds.), supra, and Ausubel, supra. Product information from manufacturers of biological reagents and experimental equipment also provide useful information. Such manufacturers include the SIGMA Chemical Company (Saint Louis, Mo.), R&D Systems (Minneapolis, Minn.), Pharmacia Amersham (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersburg, Md.), Fluka Chemica-Biochemika Analytika (Fluka Chemie AG, Buchs, Switzerland), Invitrogen (Carlsbad, Calif.), and Applied Biosystems (Foster City, Calif.), as well as many other commercial sources. Nucleic acids can also be prepared by amplification methods. Amplification methods include but are not limited to polymerase chain reaction (PCR), ligase chain reaction (LCR), transcription-based amplification system (TAS), and the self-sustained sequence replication system (3SR). A wide variety of cloning methods, host cells, and in vitro amplification methodologies are well known.

In some examples, it may only be necessary to introduce the ERRγ genetic or protein elements into certain cells or tissues. For example, introducing ERRγ into only the muscle, such as skeletal or cardiac muscle (or even a particular muscle), may be sufficient. However, in some instances, it may be more therapeutically effective and simple to treat all of the patient's cells, or more broadly disseminate the ERRγ nucleic acid or protein, for example by intravascular administration.

Nucleic acids encoding ERRγ can be introduced into the cells of a subject using routine methods, such as by using recombinant viruses (e.g., viral vectors) or by using naked DNA or DNA complexes (non-viral methods). Thus, in some embodiments, a method of increasing ERRγ activity in persons suffering from, or at risk for, a vascular disease, mitochondrial disease, and/or muscle performance disease, is achieved by introducing a nucleic acid molecule coding for ERRγ into the person. A general strategy for transferring genes into donor cells is disclosed in U.S. Pat. No. 5,529,774. The nucleic acid encoding ERRγ can be administered to the subject by any method which allows the recombinant nucleic acid to reach the appropriate cells. Exemplary methods include injection, infusion, deposition, implantation, and topical administration. Injections can be intradermal, intramuscular, iv, or subcutaneous.

In one example, an ERRγ coding sequence is introduced into a subject in a non-infectious form, such as naked DNA or liposome encapsulated DNA. Such molecules can be introduced by injection (such as intramuscular, iv, ip, pneumatic injection, or a gene gun), or other routine methods (such as oral or nasal). In one example, ERRγ coding sequence is part of a lipoplex,.dendrimer, or inorganic nanoparticle to assist in its delivery.

In one example, viral vectors are used. Generally, such methods include cloning an ERRγ coding sequence into a viral expression vector, and that vector is then introduced into the subject to be treated. The virus infects the cells, and produces the ERRγ protein sequence in vivo, where it has its desired therapeutic effect. The nucleic acid sequence encoding ERRγ can be placed under the control of a suitable promoter. Suitable promoters which may be employed include, but are not limited to, the gene's native promoter; retroviral LTR promoter; adenoviral promoters, such as the adenoviral major late promoter; the cytomegalovirus (CMV) promoter; the Rous Sarcoma Virus (RSV) promoter; inducible promoters, such as the MMTV promoter; the metallothionein promoter; heat shock promoters; the albumin promoter; the histone promoter; the β-actin promoter; TK promoters; B19 parvovirus promoters; and the ApoAI promoter.

Exemplary viral vectors include, but are not limited to: pox viruses, recombinant vacciniavirus, retroviruses (such as lentivirus), replication-deficient adenovirus strains, adeno-associated virus, herpes simplex virus, or poliovirus.

Adenoviral vectors may include essentially the complete adenoviral genome. Alternatively, the adenoviral vector may be a modified adenoviral vector in which at least a portion of the adenoviral genome has been deleted. In one embodiment, the vector includes an adenoviral 5' ITR; an adenoviral 3' ITR; an adenoviral encapsidation signal; a DNA sequence encoding a therapeutic agent such as EDA1-II, dl or DL; and a promoter for expressing the DNA sequence encoding a therapeutic agent. The vector is free of at least the majority of adenoviral E1 and E3 DNA sequences, but is not necessarily free of all of the E2 and E4 DNA sequences, and DNA sequences encoding adenoviral proteins transcribed by the adenoviral major late promoter. Such a vector may be constructed according to standard techniques, using a shuttle plasmid which contains, beginning at the 5' end, an adenoviral 5' ITR, an adenoviral encapsidation signal, and an E1a enhancer sequence; a promoter (which may be an adenoviral promoter or a foreign promoter); a tripartite leader sequence, a multiple cloning site (which may be as herein described); a poly A signal; and a DNA segment which corresponds to a segment of the adenoviral genome. The DNA segment serves as a substrate for homologous recombination with a modified or mutated adenovirus, and may encompass, for example, a segment of the adenovirus 5' genome no longer than from base 3329 to base 6246. The plasmid may also include a selectable marker and an origin of replication. The origin of replication may be a bacterial origin of replication. A desired DNA sequence encoding a therapeutic agent may be inserted into the multiple cloning site of the plasmid. The plasmid may be used to produce an adenoviral vector by homologous recombination with a modified or mutated adenovirus in which at least the majority of the E1 and E3 adenoviral DNA sequences have been deleted. Homologous recombination may be effected through co-transfection of the plasmid vector and the modified adenovirus into a helper cell line, such as 293 cells, by $CaPO_4$ precipitation. The homologous recombination produces a recombinant adenoviral vector which includes DNA sequences derived from the shuttle plasmid between the Not I site and the homologous recombination fragment, and DNA derived from the E1 and E3 deleted adenovirus between the homologous recombination fragment and the 3' ITR.

In one embodiment, the viral vector is a retroviral vector. Examples of retroviral vectors which may be employed include, but are not limited to, Moloney Murine Leukemia Virus, spleen necrosis virus, and vectors derived from retroviruses such as Rous Sarcoma Virus, Harvey Sarcoma Virus, avian leukosis virus, human immunodeficiency virus, lentivirus, myeloproliferative sarcoma virus, and mammary tumor virus. The vector can be a replication defective retrovirus particle. Retroviral vectors are useful as agents to effect retroviral-mediated gene transfer into eukaryotic cells. Retroviral vectors are generally constructed such that the majority of sequences coding for the structural genes of the virus are deleted and replaced by the gene(s) of interest. Most often, the structural genes (e.g., gag, pol, and env), are removed from the retroviral backbone using genetic engineering techniques known in the art. An ERRγ coding sequence can be incorporated into a proviral backbone using routine methods. In the most straightforward constructions, the structural genes of the retrovirus are replaced by a ERRγ gene which then is transcribed under the control of the viral regulatory sequences within the long terminal repeat (LTR). Retroviral vectors have also been constructed which can introduce more than one gene into target cells. Usually, in such vectors one gene is under the regulatory control of the viral LTR, while the second gene is expressed either off a spliced message or is under the regulation of its own, internal promoter. Alternatively, two genes may be expressed from a single promoter by the use of an Internal Ribosome Entry Site.

In one example, the viral vector is an adeno-associated virus (AAV). Gene therapy vectors using AAV can infect both dividing and non-dividing cells and persist in an extrachromosomal state without integrating into the genome of the host cell. In some examples, the rep and cap are removed from the DNA of the AAV. The ERRγ coding sequence together with a promoter to drive transcription is inserted between the inverted terminal repeats (ITR) that aid in concatamer formation in the nucleus after the single-stranded vector DNA is converted by host cell DNA polymerase complexes into double-stranded DNA.

The viral particles are administered in an amount effective to produce a therapeutic effect in a host. The exact dosage of viral particles to be administered is dependent upon a variety of factors, including the age, weight, and sex of the patient to be treated, and the nature and extent of the disease or disorder to be treated. The viral particles may be administered as part of a preparation having a titer of viral particles of at least $1\times10^5$ pfu/ml, at least $1\times10^6$ pfu/ml, at least $1\times10^7$ pfu/ml, at least $1\times10^8$ pfu/ml, at least $1\times10^9$ pfu/ml, or at least $1\times10^{10}$ pfu/ml, and in some examples not exceeding $2\times10^{11}$ pfu/ml. The viral particles can be administered in combination with a pharmaceutically acceptable carrier, for example in a volume up to 10 ml. The pharmaceutically acceptable carrier may be, for example, a liquid carrier such as a saline solution, protamine sulfate or Polybrene.

Agonists

An ERRγ agonist is an agent that induces or increases ERRγ activity or expression. Agonists of ERRγ are commercially available, and can be generated using routine methods. In some examples, the agonist is an agonist of ERRγ, but not ERRα or ERRβ. In some examples, the agonist is an agonist of ERRγ, as well as of ERRα and/or ERRβ.

ERRγ agonists are known in the art, and additional ERRγ agonists can be identified using known methods (e.g., see Zuercher et al., 2005, *J. Med. Chem.* 48(9):3107-9; Coward et al. 2001, *Proc Natl Acad Sci USA*. 8(15):8880-4; and Zhou et al., 1998, *Mol. Endocrin.* 12:1594-1604).

For example, phenolic acyl hydrazones GSK4716 (e.g., Santa Cruz Catalog #sc-203986) and GSK9089 (also known as DY131, see for example, U.S. Pat. No. 7,544,838) (N-[(E)-[4-(diethylamino)phenyl]methylideneamino]-4-hydroxy-benzamide; e.g., Tocris Bioscience Catalog #2266 or Santa Cruz Catalog #sc203571) are agonists of ERRβ and ERRγ.

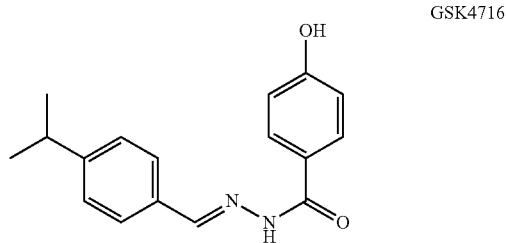

GSK4716

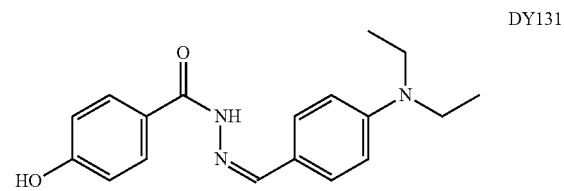

DY131

Kim et al. (*J. Comb. Chem.* 11:928-37, 2009) disclose a screening assay for agonists of ERRγ derived from GSK4716. Such a screening method can also be used to identify other agonists of ERRγ. E6 was discovered as being selective for ERRγ but not ERRα and β.

E6

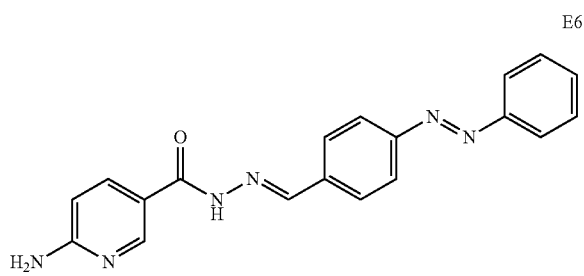 [SMILES: Nc1ccc(C(=O)N/N=C/c2ccc(/N=N/c3ccccc3)cc2)cn1]

U.S. Pat. Nos. 7,544,838 and 8,044,241 also provide ERRγ agonists that can be used with the disclosed methods, such as DY131. In addition, DY159, DY162, DY163 and DY 164 were also observed to activate ERRγ (and ERRα and β), for example in the presence of PGC-1a.

US Patent Application Publication Nos. 2011/0218196 and 2009/0281191 also provide ERRγ agonists that can be used with the disclosed methods.

Subjects

Exemplary subjects that can benefit from the disclose therapies include human and veterinary mammalian subjects, such as cats, dogs, horses, rodents, and the like. In one example, the subject treated has, or is at risk for developing, a vascular disease, mitochondrial disease, and/or muscle performance disease. Thus, such therapies can be used to prevent or treat the disease provided herein. In some examples the patient is at risk for such diseases due to smoking, alcoholism, diabetes (e.g., diabetes mellitus), obesity, head trauma, hypertension, stroke, heart attack, dyslipidemia, atherosclerosis, sedentary lifestyle, inability to exercise, and the like, and thus such patients can be treated using the methods provided herein.

In one example, the subject has or is at risk to develop a vascular disease that can be treated or prevented by increased blood flow. In one example, the vascular disease is a cerebrovascular disease, such as a vascular disease of the brain. Exemplary diseases that can be treated or prevented by increased blood flow in or to the brain include migraines, dementia, and ischemia, such as ischemia resulting from or due to ischemic stroke, transient ischemic attacks (TIAs), and carotid stenosis. In some examples such patients are diabetic, smokers, have hypertension, sedentary, or have suffered head trauma.

In one example, the vascular disease is a cardiovascular disease, such as a vascular disease of the heart or blood vessels. Exemplary diseases that can be treated or prevented by increased blood flow in the heart or vessels include ischemic heart disease, coronary heart disease, and cardiomyopathy. In some examples such patients are diabetic, smokers, have hypertension, have suffered a heart attack, or are sedentary.

In one example, the vascular disease is a vascular disease of the kidney. Exemplary diseases that can be treated or prevented by increased blood flow in the kidney include kidney failure. In some examples such patients are diabetic, smokers, have hypertension, or are sedentary.

In one example, the vascular disease is a vascular disease of the brown adipose tissue. Exemplary diseases that can be treated or prevented by increased blood flow in the brown adipose tissue include obesity. In some examples such patients are diabetic, smokers, have hypertension, or are sedentary.

In one example, the vascular disease is a vascular disease of the skeletal muscle. Exemplary diseases that can be treated or prevented by increased blood flow in the skeletal muscle include peripheral vascular or artery disease, muscle atrophy, muscle wasting and sarcopenia. In some examples such patients are diabetic, smokers, have hypertension, or are sedentary.

In one example, the subject has or is at risk to develop a mitochondrial disease that can be treated or prevented by increased mitochondrial activity. Exemplary mitochondrial diseases that can be treated or prevented by increased mitochondrial activity include muscle disease (such as muscle atrophy, muscle wasting and sarcopenia), diabetes mellitus and deafness (DAD), hearing loss, Leber's hereditary optic neuropathy (LHON), Leigh syndrome, neuropathy, ataxia, retinitis pigmentosa, and ptosis (NARP), myoneurogenic gastrointestinal encephalopathy (MNGIE), myoclonic epilepsy with ragged red fibers (MERRF) progressive myoclonic epilepsy, mitochondrial myopathy, encephalomyopathy, lactic acidosis, stroke-like symptoms (MELAS), and mitochondrial neurogastrointestinal encephalomyopathy (MNGIE). In some examples such patients are sedentary.

In one example, the subject has or is at risk to develop a skeletal or cardiac muscle disease that can be treated or prevented by increased muscle performance. Exemplary muscle diseases that can be treated or prevented by muscle rehabilitation, such as increased muscle performance, include muscle disease (such as muscle atrophy, muscle wasting and sarcopenia, and heart disease). In some examples such patients are diabetic, smokers, have hypertension, or are sedentary.

Muscle atrophy, or disuse atrophy, is a decrease in the mass of the muscle; it can be a partial or complete wasting away of muscle. When a muscle atrophies, this leads to muscle weakness. Muscle atrophy can result from cancer, AIDS, congestive heart failure, COPD (chronic obstructive pulmonary disease), renal failure, severe burns, Dejerine Sottas syndrome (HSMN Type III), inactivity (e.g., when a cast is put on a limb), weightlessness (e.g., due to spaceflight), extended bedrest (e.g., during a prolonged illness), cachexia, liver failure, starvation, and disuse. Thus, the disclosed methods can be used to treat or prevent atrophy resulting from such conditions.

Sarcopenia refers to the process during aging, where there is a gradual decrease in the ability to maintain skeletal muscle function and mass.

In addition to the simple loss of muscle mass (atrophy), or the age-related decrease in muscle function (sarcopenia), other muscle diseases which may be caused by structural defects in the muscle (muscular dystrophy), or by inflammatory reactions in the body directed against muscle (the myopathies) can be treated using the disclosed methods.

Administration of Agents that Increase ERRγ Activity

Compositions that include one or more agents that increase ERRγ activity, such as ERRγ nucleic acids, ERRγ proteins, and ERRγ agonists that can be used to increase vascularization, mitochondrial activity, and/or muscle performance, are suited for the preparation of pharmaceutical compositions.

Pharmaceutical compositions that include one or more agents that increase ERRγ activity are provided. These pharmaceutical compositions can be used in methods of treatment/prevention of vascular, mitochondrial, and muscular disorders, and can be formulated with an appropriate physiologically acceptable solid or liquid carrier, depending upon the particular mode of administration chosen. A variety of aqueous carriers can be used, for example, buffered saline and the like. These solutions are sterile and generally free of undesirable matter. These compositions can be sterilized by conventional, well known sterilization techniques. The compositions can contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of antibody in these formulations can vary widely, and will be selected primarily based on fluid volumes, viscosities, body weight and the like in accordance with the particular mode of administration selected and the subject's needs. Compositions including one or more agents that increase ERRγ activity are of use, for example, for the treatment of a vascular, mitochondrial, or muscular disorders, such as those resulting from inactivity. The pharmaceutically acceptable carriers and excipients useful in this disclosure, for either therapeutic or diagnostic methods, are conventional. The one or more agents that increase ERRγ activity can be formulated for systemic or local (such as inhalational) administration. In one example, the one or more agents that increase ERRγ activity is formulated for parenteral administration, such as intravenous or intramuscular administration. For instance, parenteral formulations usually include injectable fluids that are pharmaceutically and physiologically acceptable fluid vehicles such as water, physiological saline, other balanced salt solutions, aqueous dextrose, glycerol or the like. Excipients that can be included are, for instance, other proteins, such as human serum albumin or plasma preparations. If desired, the pharmaceutical composition to be administered can also contain minor amounts of non-toxic auxiliary substances, such as wetting or emulsifying agents, preservatives, and pH buffering agents and the like, for example sodium acetate or sorbitan monolaurate.

The compositions can be prepared in unit dosage forms for administration to a subject. The dosage form of the pharmaceutical composition will be determined by the mode of administration chosen. For instance, in addition to injectable fluids, topical, inhalation, oral and suppository formulations can be employed. Topical preparations can include ointments, sprays and the like. Inhalation preparations can be liquid (such as solutions or suspensions) and include mists, sprays and the like. Oral formulations can be liquid (for example, syrups, solutions or suspensions), or solid (such as powders, pills, tablets, or capsules). Suppository preparations can also be solid, gel, or in a suspension form. For solid compositions, conventional non-toxic solid carriers can include pharmaceutical grades of mannitol, lactose, starch, or magnesium stearate. Actual methods of preparing such dosage forms are known, or will be apparent, to those skilled in the art.

The pharmaceutical compositions that include one or more agents that increase ERRγ activity can be formulated in unit dosage form suitable for individual administration of precise dosages. In addition, the pharmaceutical compositions may be administered in a single dose or as in a multiple dose schedule. A multiple dose schedule is one in which a primary course of treatment may be with more than one separate dose, for instance 1-10 doses, followed by other doses given at subsequent time intervals as needed to maintain or reinforce the action of the compositions. Treatment can involve daily or multi-daily doses of compound(s) over a period of a few days to months, or even years. Thus, the dosage regime will also, at least in part, be determined based on the particular needs of the subject to be treated, the severity of the affliction, whether the therapeutic agent is administered for preventive or therapeutic purposes, previous prophylaxis and therapy, the subject's clinical history and response to the therapeutic agent, and the manner of administration, and can be left to the judgment of the prescribing clinician. Within these bounds, the formulation to be administered will contain a quantity of the active component(s) in amounts effective to achieve the desired effect in the subject being treated. A therapeutically effective amount of one or more agents that increase ERRγ activity is one that which provides either subjective relief of a symptom(s) or an objectively identifiable improvement as noted by the clinician or other qualified observer. These compositions can be administered in conjunction with another agent, such as angiogenic therapy (e.g., those that include a VEGF, such as VEGF-A), either simultaneously or sequentially. The one or more agents that increase ERRγ activity also can be used or administered as a mixture, for example in equal amounts, or individually, provided in sequence, or administered all at once.

Single or multiple administrations of the compositions can be administered depending on the dosage and frequency as required and tolerated by the subject. The composition should provide a sufficient quantity of one or more agents that increase ERRγ activity to effectively treat the subject or inhibit the development of the desired disease. The dosage can be administered once but can be applied periodically until either a therapeutic result is achieved or until side effects warrant discontinuation of therapy. In one example, a dose of the one or more agents that increase ERRγ activity is infused for thirty minutes every other day. In this example, about one to about ten doses can be administered, such as three or six doses can be administered every other day. In a further example, a continuous infusion is administered for about five to about ten days. The subject can be treated at regular intervals, such as monthly, until a desired therapeutic result is achieved. Generally, the dose is sufficient to treat or ameliorate symptoms or signs of a disease without producing unacceptable toxicity to the patient.

In one specific, non-limiting example, a unit dosage for intravenous or intramuscular administration of an ERRγ agonist includes at least 0.5 μg agonist per dose, such as at least 5 μg agonist per dose, at least 50 μg agonist per dose, or at least 500 μg agonist per dose. In some examples, doses are administered three-times in one week.

In one specific, non-limiting example, an ERRγ agonist daily dosage is from about 0.01 milligram to about 500 milligram per kilogram of animal body weight, for example given as a single daily dose or in divided doses two to four times a day, or in sustained release form. For most large mammals, the total daily dosage is from about 0.01 milligrams to about 100 milligrams per kilogram of body weight, such as from about 0.5 milligram to about 100 milligrams per kilogram of body weight, which can be administered in divided doses 2 to 4 times a day in unit dosage form containing for example from about 10 to about 100 mg of the compound in sustained release form. In one example, the daily oral dosage in humans is between 1 mg and 1 g, such as between 10 mg and 500 mg, 10 mg and 200 mg, such as 10 mg. The dosage regimen may be adjusted within this range or even outside of this range to provide the optimal therapeutic response. Oral administration of an ERRγ agonist can be carried out using tablets or capsules, such as about 10 mg to about 500 mg of the ERRγ agonist. Exemplary doses in tablets include 0.1 mg, 0.2 mg, 0.25 mg, 0.5 mg, 1 mg, 2 mg, 5 mg, 10 mg, 25 mg, 50 mg, 100 mg, 250 mg, and 500 mg of the ERRγ agonist. Other oral forms can also have the same dosages (e.g., capsules). In one example, a dose of an ERRγ agonist administered parenterally is at least 10 mg, such as 10 to 500 mg or 10 to 200 mg of the ERRγ agonist.

In one specific, non-limiting example, a unit dosage for oral administration such as a table or capsule), or for oral intravenous or intramuscular administration, of an ERRγ protein includes about 1 μg to 1000 mg of ERRγ protein per dose, such as 1 μg to 100 μg ERRγ protein per dose, 1 μg to 500 μg ERRγ protein per dose, 1 μg to 1 mg ERRγ protein per dose, 1 mg to 1000 mg ERRγ protein per dose, or 10 mg to 100 mg ERRγ protein per dose. In some examples, doses are administered at least three-times in one week.

In one specific, non-limiting example, a unit dosage for administration of an ERRγ nucleic acid (such as injection, gene gun, pneumatic injection, or topical) includes at least 10 ng, at least 100 ng, at least 1 μg, at least 10 μg, at least 100 μg, or at least 500 μg nucleic acid per dose. Saline injections can use amounts of DNA, such as from 10 μg-1 mg, whereas gene gun deliveries can require 100 to 1000 times less DNA than intramuscular saline injection (such as 0.2 μg-20 μg). These amounts can vary from species to species, with mice, for example, requiring approximately 10 times less DNA than primates. Saline injections may require more DNA because the DNA is delivered to the extracellular spaces of the target tissue (e.g., muscle), where it has to overcome physical barriers before it is taken up by the cells, while gene gun deliveries bombard. DNA directly into the cells.

In one specific, non-limiting example, a unit dosage for intravenous or intramuscular administration of a viral vector that encodes ERRγ includes at least $1\times10^8$ viral particles per dose, such as at least $1\times10^9$ viral particles per dose, at least $1\times10^{10}$ viral particles per dose, or at least $1\times10^{11}$ viral particles per dose.

Actual methods for preparing administrable compositions will be known or apparent to those skilled in the art and are described in more detail in such publications as *Remington's Pharmaceutical Science*, 19th ed., Mack Publishing Company, Easton, Pa. (1995).

Agents that increase ERRγ activity (such as a ERRγ protein or agonist) can be provided in lyophilized form and rehydrated with sterile water before administration, although they are also provided in sterile solutions of known concentration. The resulting solution can then added to an infusion bag containing 0.9% sodium chloride, USP, and can be administered in some examples at a dosage of from 1 to 300 mg/kg of body weight. Considerable experience is available in the art in the administration of proteins or nucleic acids. Such molecules can be administered by slow infusion, rather than in an intravenous push or bolus. In one example, a higher loading dose is administered, with subsequent, maintenance doses being administered at a lower level.

The agents that increase ERRγ can be administered to humans or other mammal using routine modes of administration, such as topically, orally, intravascularly such as intravenously, intramuscularly, intraperitoneally, intranasally, intradermally, intrathecally, subcutaneously, intracraneally, via inhalation or via suppository. The particular mode of administration and the dosage regimen will be selected by the attending clinician, taking into account the particulars of the case (for example the subject, the disease, the disease state involved, and whether the treatment is prophylactic).

Controlled release parenteral formulations of agents that increase ERRγ activity can be made as implants, oily injections, or as particulate systems. For a broad overview of protein delivery systems (see Banga, A. J., *Therapeutic Peptides and Proteins: Formulation, Processing, and Delivery Systems*, Technomic Publishing Company, Inc., Lancaster, Pa., 1995). Particulate systems include microspheres, microparticles, microcapsules, nanocapsules, nanospheres, and nanoparticles. Microcapsules contain the therapeutic protein as a central core. In microspheres the therapeutic is dispersed throughout the particle. Particles, microspheres, and microcapsules smaller than about 1 μm are generally referred to as nanoparticles, nanospheres, and nanocapsules, respectively. Capillaries have a diameter of approximately 5 μm so that only nanoparticles are administered intravenously. Microparticles are typically around 100 μm in diameter and are administered subcutaneously or intramuscularly (see Kreuter, J., *Colloidal Drug Delivery Systems*, J. Kreuter, ed., Marcel Dekker, Inc., New York, N.Y., pp. 219-342, 1994; Tice & Tabibi, *Treatise on Controlled Drug Delivery*, A. Kydonieus, ed., Marcel Dekker, Inc. New York, N.Y., pp. 315-339, 1992).

Polymers can be used for ion-controlled release. Various degradable and nondegradable polymeric matrices for use in controlled drug delivery are known in the art (Langer, R., *Accounts Chem. Res.* 26:537, 1993). For example, the block copolymer, polaxamer 407 exists as a viscous yet mobile liquid at low temperatures but forms a semisolid gel at body temperature. It has shown to be an effective vehicle for formulation and sustained delivery of recombinant interleukin-2 and urease (Johnston et al., *Pharm. Res.* 9:425, 1992; and Pec et al., *J. Parent. Sci. Tech.* 44:58, 1990). Alternatively, hydroxyapatite has been used as a microcarrier for controlled release of proteins (Ijntema et al., *Int. J. Pharm.* 112:215, 1994). In yet another aspect, liposomes are used for controlled release as well as drug targeting of the lipid-capsulated drug (Betageri, et al., Liposome Drug Delivery Systems, Technomic Publishing Co., Inc., Lancaster, Pa., 1993). Numerous additional systems for controlled delivery of therapeutic proteins are known (see, for example, U.S. Pat. Nos. 5,055,303, 5,188,837, 4,235,871, 4,501,728, 4,837,028 4,957,735 and 5,019,369, 5,055,303; 5,514,670; 5,413,797; 5,268,164; 5,004,697; 4,902,505; 5,506,206, 5,271,961; 5,254,342 and 5,534,496).

Site-specific administration of the agents that increase ERRγ activity can be used, for instance by applying the agent to a region of the body in need of treatment, such as the brain, particular muscle, or kidney. In some embodiments, sustained release of the pharmaceutical preparation that includes a therapeutically effective amount of the one or more agents that increase ERRγ activity may be beneficial.

The present disclosure also includes combinations of one or more agents that increase ERRγ activity with one or more other agents useful in the treatment of a vascular, mitochondria, or muscular disorder. For example, the compounds of this disclosure can be administered in combination with effective doses of other angiogenic agents, such as vascular endothelial growth factor (VEGF), or fibroblast growth factor (FGF). The term "administration in combination" or "co-administration" refers to both concurrent and sequential administration of the active agents.

The following examples are provided to illustrate certain particular features and/or embodiments. These examples should not be construed to limit the disclosure to the particular features or embodiments described.

EXAMPLE 1

Materials and Methods

This example describes the materials and methods used for Examples 2-8.

Animals. Mouse ERRγ cDNA was placed downstream to the human α-skeletal actin promoter and upstream of the SV40 intron/poly (A) sequence. The purified transgene was injected into C57BL/6J×CBA F1 zygotes. Two transgenic founders (TG 425 and 421) were obtained that were back-crossed for 5 generations with C57BL/6J. All experiments used age (2-3 months) and sex (male) matched transgenic and wild type (WT) littermates. Mice were maintained on a normal chow diet. ERRγ +/- mice and tissue β-galactosidase staining has been described previously (Alaynick et al., 2007).

Drug treatment. Male C57B1/6J mice (8 weeks old) were intra-peritoneally injected with vehicle or AICAR (500 mg/kg/day), as previously described (Narkar et al., 2008).

Gene and protein expression analysis. RNA was extracted using the TRIZOL ® extraction method from quadriceps or soleus isolated from WT and transgenic mice. Additionally, protein lysates were prepared from quadriceps and analyzed by western blotting with myoglobin (Dako), CYCS (Santacruz), UCP3 (Affinity Bioreagents), phospho-AMPK alpha (Cell Signaling, Cat no #2535) and total-AMPK alpha (Cell Signaling, Cat no #2532) antibodies. The AMPK antibodies detect both the alpha 1 and 2 catalytic subunits of AMPK (Narkar et al., 2008).

Microarray Analysis. Global gene expression analysis was performed in quadriceps from WT and transgenic mice, as previously described (Narkar et al., 2008).

Fluorescence Micro-angiography. Blood vessel mapping was performed as previously described (Johnson et al., 2004; Springer et al., 2000). Briefly, a red fluorescent microsphere (0.1 µM) suspension was intra-ventricularly perfused (10 ml, 1 ml/min) followed by euthanasia and tissue collection. Longitudinal cryo-sections (10 µM) of frozen gastrocnemius were processed and subjected to confocal microscopy to image skeletal muscle vasculature.

Cell culture, in vitro angiogenesis and Vegfa ELISA. C2C12 myoblasts were grown in 20% FBS-DMEM and differentiated in 2% horse serum-DMEM [with penicillin/streptomycin]. Conditioned media from two day differentiated WT and ERR/over-expressing C2C12 myotubules were used in the in vitro angiogenesis assay. Murine endothelial SVEC4-10 cells were cultured and maintained in DMEM containing 10% fetal bovine serum and penicillin/streptomycin. On the day of the experiment $4 \times 10^5$ cells/500 µl/well were plated in matrigel-coated 12-well plates. The cells were immediately treated for 7 hr with C2C12 cell conditioned media (2500), followed by evaluation of tube formation. Vegfa concentration in the conditioned media was measured using commercial Elisa kit according manufacturer's instructions [Research & Diagnostics].

Oxymetery and treadmill assays. Oxygen consumption, respiratory exchange ratio and ambulatory activity were measured in 3 month old, WT and transgenic male mice (N=6-7/group) of comparable weight using Comprehensive Lab Animal Monitoring System to obtain oxymetric measurements (Columbus Instruments). These mice were first acclimated in the monitoring system for 1 day, followed by data collection for 24 hr to include a 12 hr light and dark cycle. For each animal, the average of all the data points within the light or dark phase was used as a representative value of the respective cycle. Diurnal differences between the light and dark cycles were detectable in all animals, validating the method of data collection.

Endurance was determined in WT and transgenic (N=6 mice/group), as previously described (Narkar et al., 2008). The treadmill endurance test was performed as follows. WT and transgenic mice were acclimated to treadmill running (8 meters/min for 15 min) every other day for 1 week before the test. For the endurance testing, the mice were run on a treadmill at 5° inclination as the speed was gradually increased to 14 meters/min. After reaching 14 m/min, mice were run to exhaustion at constant speed. Endurance was measured as the function of time and distance ran.

Succinate Dehydrogenase (SDH) Staining. SDH staining was performed on 6 µM cryo-sections of gastrocnemius. Briefly, WT and transgenic sections were incubated at 37° C. for 10 min in substrate buffer [0.2M Phosphate buffer containing sodium succinate (250 mg/10 ml) and NBT (10 mg/10 ml)]. Following incubation, sections were washed three times with water following by two washes each with increasing and decreasing concentrations of acetone (30%, 60%, 90%). Finally, the sections were washed three times with water and mounted in an aqueous mounting media.

Immunohistochemistry. Gastrocnemius muscles isolated from WT and transgenic mice were equilibrated in 30% sucrose (in PBS) for 2-3 hr and frozen in OCT. Cryo-sections (10[1M) were fixed (4% paraformaldehyde-PBS), permeabilized(0.3% TRITON X® detergent-PBS) and blocked (normal goat serum-PBS) before antibody treatment. Further, the sections were incubated overnight at 4° C. with anti-PECAM 1 antibody (1:25 in PBS, SEROTEC), washed three times with PBS, incubated with anti-rat secondary antibody (1:250, ALEXA FLOR® 344 dye), washed three times with PBS and mounted in VECTASHIELD® mounting medium. For negative controls, primary antibody was replaced with normal goat serum-PBS for overnight incubation.

Alkaline phosphatase (AP) staining. For AP staining, 10 µM muscle sections were fixed in ice-cold acetone (5 min, -20° C.), incubated in Tris-buffered Naphthol AS-MX phosphate/ N,N Dimethylformamide solution (30 min, 37° C.), rinsed with distilled water (3×2 min) and mounted with aqueous media.

Data Analysis. Data was analyzed using either one way ANOVA with an appropriate post hoc test, or unpaired student's t-test, as indicated.

The global gene expression data has been deposited in the NCBI Gene Expression Omnibus under the GEO series accession number (pending).

EXAMPLE 2

Skeletal Muscle ERRγ Expression

This example describes methods used to examine ERRγ expression in skeletal muscle.

Because skeletal muscle is a functionally heterogeneous tissue containing both aerobic slow-twitch and glycolytic fast-twitch muscles, ERRγ expression was evaluated in the context of different myofibrillar beds. The ERRγ transcript was highly expressed in oxidative muscles such as soleus and red gastrocnemius, with minimal expression in glycolytic quadriceps and white gastrocnemius (FIG. 1A, lower panel). ERRγ protein is undetectable in quadriceps, but highly expressed in soleus (FIG. 1A, upper panel).

Figure 1B:
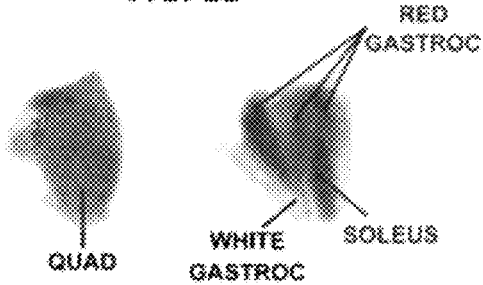

Viable ERRγ +/-mice are available in which a β-galactosidase protein-coding region without the promoter was introduced in-frame with the initiation site of the Esrrg gene (Alaynick et al., 2007) such that the enzyme mimics the expression of endogenous ERRγ. β-Galactosidase staining of different muscle beds from ERRγ +/-adult mice confirmed that the receptor is highly expressed in oxidative (e.g., soleus and red gastrocnemius) compared to the minimal levels in glycolytic muscles (e.g., quadriceps, white gastrocnemius) (FIG. 1B).

EXAMPLE 3

Transgenic Muscle-Specific ERRγ Over-Expression

This example describes methods used to demonstrate the role of ERRγ in oxidative and slow-twitch muscle biology.

Figure 1D:
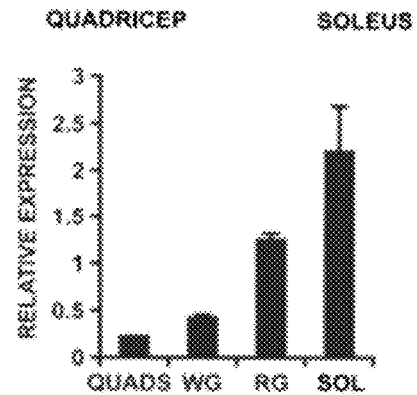
Figure 1D:
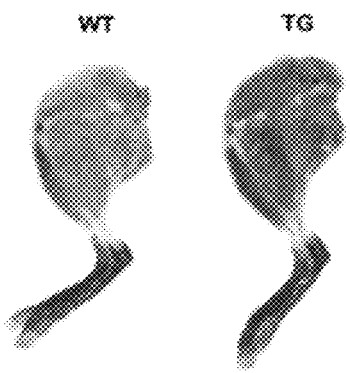
Figure 1C:
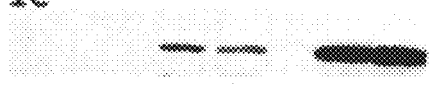
Figure 1E:
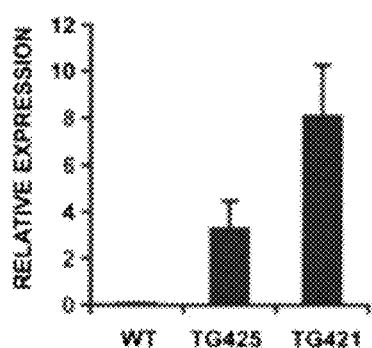
Figure 1E:
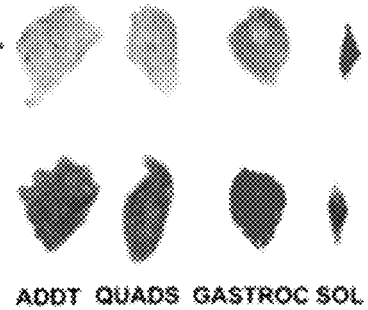

Transgenic mice were generated that selectively expressed ERRγ in skeletal muscles under the control of the human alpha-skeletal actin promoter (Muscat and Kedes, 1987; Wang et al., 2004). Two ERRγ over-expressing (ERRGO) transgenic lines were obtained (TG 421 and 425) showing both transcript (lower panel) and protein (upper panel) in fast-twitch quadriceps (FIG. 1C). Gross anatomical analysis of hindlimb muscles (FIG. 1D) and dissection of individual muscle beds (FIG. 1E) revealed enhanced red coloration (characteristic of oxidative fibers) in transgenic compared to wild type muscle. Importantly, slow-twitch (soleus) muscle, already high in ERRγ expression, was not affected (FIG. 1E), presumably because it is already fully oxidative. In addition, oxidative biomarkers myoglobin and cytochrome c were induced in the quadriceps of both the transgenic lines compared to wild type mice (FIG. 1F). TG 421 was used in later experiments due to slightly higher biomarker expression in this progeny.

EXAMPLE 4

Fast to Slow-Twitch Transformation of Skeletal Muscle by ERRγ

This example describes methods used to determine the transcriptional effect of ERRγ by measuring muscle gene expression in quadriceps from wild type and ERRGO mice.

In gene array analysis, it was observed that ERRγ regulated 1123 genes in skeletal muscles, of which 623 genes were induced. Gene ontology-based classification of these genes is presented in FIG. 2A. The majority of the up-regulated genes belong to either mitochondrial biology (90) or oxidative metabolism (43) encoding various components of fatty acid oxidation pathway as well as the oxidative respiratory chain reflective of aerobic adaptation (Table 1).

TABLE 1

Global gene expression was compared between wild type and ERRγ transgenic quadriceps. The positively regulated genes were subjected to gene ontology classification. The genes linked to mitochondrial respiration and/or fatty acid oxidation are described below (N = 3, each pooled from 3 mice, $p < 0.05$, Bonferroni's multiple comparison test).

| Locus | Fold | Description |
|---|---|---|
| 1300010F03Rik | 2.135 | RIKEN cDNA 1300010F03 gene |
| 1700020C11Rik | 2.604 | RIKEN cDNA 1700020C11 gene |
| 1700034H14Rik | 1.742 | RIKEN cDNA 1700034H14 gene |
| Acaa1a | 2.169 | acetyl-Coenzyme A acyltransferase 1A |
| Acaa2 | 3.473 | acetyl-Coenzyme A acyltransferase 2 (mitochondrial 3-oxoacyl-Coenzyme A thiolase) |
| Acadl | 2.093 | acyl-Coenzyme A dehydrogenase, long-chain |
| Acadm | 1.931 | acyl-Coenzyme A dehydrogenase, medium chain |
| Acads | 1.713 | acyl-Coenzyme A dehydrogenase, short chain |
| Acadvl | 2.2 | acyl-Coenzyme A dehydrogenase, very long chain |
| Acat1 | 1.943 | acetyl-Coenzyme A acetyltransferase 1 |
| Acot1 | 2.031 | acyl-CoA thioesterase 1 |
| Acot11 | 2.356 | acyl-CoA thioesterase 11 |
| Acot2 | 3.018 | acyl-CoA thioesterase 2 |
| Acot7 | 1.952 | acyl-CoA thioesterase 7 |
| Acsl1 | 2.564 | acyl-CoA synthetase long-chain family member 1 |
| Adh1 | 1.843 | alcohol dehydrogenase 1 (class I) |
| Ak3l1 | 7.733 | adenylate kinase 3 alpha-like 1 |
| Akap1 | 2.569 | A kinase (PRKA) anchor protein 1 |
| Aldh2 | 2.484 | aldehyde dehydrogenase 2, mitochondrial |
| Atad3a | 1.78 | ATPase family, AAA domain containing 3A |
| Atp5h | 1.685 | ATP synthase, H+ transporting, mitochondrial F0 complex, subunit d |
| Bcat2 | 1.793 | branched chain aminotransferase 2, mitochondrial |
| Bdh1 | 2.899 | 3-hydroxybutyrate dehydrogenase, type 1 |
| Cabc1 | 5.199 | chaperone, ABC1 activity of bc1 complex like (*S. pombe*) |
| Cat | 1.919 | catalase |
| Cds2 | 1.854 | CDP-diacylglycerol synthase (phosphatidate cytidylyltransferase) 2 |
| Chkb | 2.021 | choline kinase beta |
| Cox15 | 1.727 | COX15 homolog, cytochrome c oxidase assembly protein (yeast) |
| Cox6a2 | 1.643 | cytochrome c oxidase, subunit VI a, polypeptide 2 |
| Cpt1b | 1.698 | carnitine palmitoyltransferase 1b, muscle |
| Cpt2 | 1.815 | carnitine palmitoyltransferase 2 |
| Ctsb | 2.539 | cathepsin B |
| D10Jhu81e | 1.709 | DNA segment, Chr 10, Johns Hopkins University 81 expressed |
| Dci | 2.037 | dodecenoyl-Coenzyme A delta isomerase (3,2 trans-enoyl-Coenyme A isomerase) |
| Decr1 | 2.745 | 2,4-dienoyl CoA reductase 1, mitochondrial |
| Dhrs4 | 2.103 | dehydrogenase/reductase (SDR family) member 4 |
| Dlat | 2.027 | dihydrolipoamide S-acetyltransferase (E2 component of pyruvate dehydrogenase complex) |
| Ech1 | 2.297 | enoyl coenzyme A hydratase 1, peroxisomal |
| Etfb | 1.695 | electron transferring flavoprotein, beta polypeptide |
| Etfdh | 1.962 | electron transferring flavoprotein, dehydrogenase |
| Fabp3 | 3.658 | fatty acid binding protein 3, muscle and heart |

TABLE 1-continued

Global gene expression was compared between wild type and ERRγ transgenic quadriceps. The positively regulated genes were subjected to gene ontology classification. The genes linked to mitochondrial respiration and/or fatty acid oxidation are described below (N = 3, each pooled from 3 mice, $p < 0.05$, Bonferroni's multiple comparison test).

| Locus | Fold | Description |
|---|---|---|
| Fdft1 | 2.287 | farnesyl diphosphate farnesyl transferase 1 |
| Gcdh | 2.246 | glutaryl-Coenzyme A dehydrogenase |
| Gfm1 | 2.099 | G elongation factor, mitochondrial 1 |
| Ggtla1 | 1.767 | gamma-glutamyltransferase-like activity 1 |
| Glrx5 | 2.036 | glutaredoxin 5 homolog (S. cerevisiae) |
| Glud1 | 1.812 | glutamate dehydrogenase 1 |
| Got2 | 2.262 | glutamate oxaloacetate transaminase 2, mitochondrial |
| Hadh | 1.969 | hydroxyacyl-Coenzyme A dehydrogenase |
| Hadha | 2.415 | hydroxyacyl-Coenzyme A dehydrogenase/3-ketoacyl-Coenzyme A thiolase/enoyl-Coenzyme A hydratase (trifunctional protein), alpha subunit |
| Hadhb | 1.775 | hydroxyacyl-Coenzyme A dehydrogenase/3-ketoacyl-Coenzyme A thiolase/enoyl-Coenzyme A hydratase (trifunctional protein), beta subunit |
| Hba-a1 | 4.779 | hemoglobin alpha, adult chain 1 |
| Herc2 | 1.786 | hect (homologous to the E6-AP (UBE3A) carboxyl terminus) domain and RCC1 (CHC1)-like domain (RLD) 2 |
| Hibadh | 1.685 | 3-hydroxyisobutyrate dehydrogenase |
| Hsdl2 | 2.283 | hydroxysteroid dehydrogenase like 2 |
| Hspa9 | 1.673 | heat shock protein 9 |
| Idh3b | 1.749 | isocitrate dehydrogenase 3 (NAD+) beta |
| Ivd | 1.843 | isovaleryl coenzyme A dehydrogenase |
| Ldhd | 2.18 | lactate dehydrogenase D |
| Lpl | 1.873 | lipoprotein lipase |
| Me3 | 1.657 | malic enzyme 3, NADP(+)-dependent, mitochondrial |
| Mfn1 | 1.855 | mitofusin 1 |
| Mlycd | 1.761 | malonyl-CoA decarboxylase |
| Mrm1 | 1.868 | mitochondrial rRNA methyltransferase 1 homolog (S. cerevisiae) |
| Mrpl14 | 2.465 | mitochondrial ribosomal protein L14 |
| Mrpl19 | 1.875 | mitochondrial ribosomal protein L19 |
| Mrpl3 | 1.744 | mitochondrial ribosomal protein L3 |
| Mrpl9 | 1.734 | mitochondrial ribosomal protein L9 |
| Msrb2 | 2.412 | methionine sulfoxide reductase B2 |
| Mterfd3 | 2.284 | MTERF domain containing 3 |
| Mtx2 | 1.738 | metaxin 2 |
| Mut | 1.666 | methylmalonyl-Coenzyme A mutase |
| Ndufab1 | 1.645 | NADH dehydrogenase (ubiquinone) 1, alpha/beta subcomplex, 1 |
| Ndufb2 | 1.734 | NADH dehydrogenase (ubiquinone) 1 beta subcomplex, 2 |
| Ndufs8 | 1.895 | NADH dehydrogenase (ubiquinone) Fe—S protein 8 |
| Ndufv1 | 1.648 | NADH dehydrogenase (ubiquinone) flavoprotein 1 |
| Nnt | 4.809 | nicotinamide nucleotide transhydrogenase |
| Nrip1 | 1.821 | nuclear receptor interacting protein 1 |
| Nudt8 | 2.662 | nudix (nucleoside diphosphate linked moiety X)-type motif 8 |
| Osbpl1a | 2.225 | oxysterol binding protein-like 1A |
| Pdk4 | 2.692 | pyruvate dehydrogenase kinase, isoenzyme 4 |
| Phca | 2.679 | phytoceramidase, alkaline |
| Pisd | 1.679 | phosphatidylserine decarboxylase |
| Pitpnc1 | 2.322 | phosphatidylinositol transfer protein, cytoplasmic 1 |
| Pla2g4b | 4.406 | phospholipase A2, group IVB (cytosolic) |
| Plcb4 | 2.431 | phospholipase C, beta 4 |
| Plcd1 | 2.009 | phospholipase C, delta 1 |
| Ppara | 2.444 | peroxisome proliferator activated receptor alpha |
| Ppif | 1.989 | peptidylprolyl isomerase F (cyclophilin F) |
| Ppm1k | 1.759 | protein phosphatase 1K (PP2C domain containing) |
| Prdx5 | 1.655 | peroxiredoxin 5 |
| Prdx6 | 1.643 | peroxiredoxin 6 |
| Qk | 1.875 | quaking |
| Rtn4ip1 | 2.032 | reticulon 4 interacting protein 1 |
| Sdhb | 1.699 | succinate dehydrogenase complex, subunit B, iron sulfur (Ip) |
| Sfxn5 | 1.992 | sideroflexin 5 |
| Slc25a20 | 2.989 | solute carrier family 25 (mitochondrial carnitine/acylcarnitine translocase), member 20 |
| Slc25a22 | 2.49 | solute carrier family 25 (mitochondrial carrier, glutamate), member 22 |
| Slc25a4 | 3.435 | solute carrier family 25 (mitochondrial carrier, adenine nucleotide translocator), member 4 |

TABLE 1-continued

Global gene expression was compared between wild type and ERRγ transgenic quadriceps. The positively regulated genes were subjected to gene ontology classification. The genes linked to mitochondrial respiration and/or fatty acid oxidation are described below (N = 3, each pooled from 3 mice, p < 0.05, Bonferroni's multiple comparison test).

| Locus | Fold | Description |
|---|---|---|
| Slc27a1 | 1.769 | solute carrier family 27 (fatty acid transporter), member 1 |
| Slc40a1 | 3.279 | solute carrier family 40 (iron-regulated transporter), member 1 |
| Sod2 | 1.766 | superoxide dismutase 2, mitochondrial |
| Sorl1 | 2.367 | sortilin-related receptor, LDLR class A repeats-containing |
| Tfam | 1.754 | transcription factor A, mitochondrial |
| Timm44 | 1.683 | translocase of inner mitochondrial membrane 44 |
| Tomm22 | 2.072 | translocase of outer mitochondrial membrane 22 homolog (yeast) |
| Txn2 | 2.021 | thioredoxin 2 |
| Ucp3 | 2.838 | uncoupling protein 3 (mitochondrial, proton carrier) |
| Ung | 3.577 | uracil DNA glycosylase |
| Uqcrq | 2.108 | ubiquinol-cytochrome c reductase, complex III subunit VII |

Furthermore, contractile genes, especially ones associated with slow myofibers, were also activated raising the possibility of fast-to-slow transformation linked to the metabolic switch (Table 2).

TABLE 2

Contractile genes induced by ERRγ in quadriceps of the transgenic mice (N = 3, each pooled from 3 mice, p < 0.05, Bonferroni's multiple comparison test).

| Locus | Fold | Description |
|---|---|---|
| Abra | 2.915 | actin-binding Rho activating protein |
| Actn2 | 4.281 | actinin alpha 2 |
| Ankrd2 | 9.885 | ankyrin repeat domain 2 (stretch responsive muscle) |
| Csrp3 | 8.534 | cysteine and glycine-rich protein 3 |
| Kcnj8 | 1.824 | potassium inwardly-rectifying channel, subfamily J, member 8 |
| Myh2 | 5.84 | myosin, heavy polypeptide 2, skeletal muscle, adult |
| Myoz2 | 3.67 | myozenin 2 |
| Nrap | 1.66 | nebulin-related anchoring protein |
| Spna2 | 1.804 | spectrin alpha 2 |
| Tnnc1 | 3.256 | troponin C, cardiac/slow skeletal |
| Tnni1 | 4.827 | troponin I, skeletal, slow 1 |
| Tnnt1 | 15 | troponin T1, skeletal, slow |
| Tpm3 | 3.49 | tropomyosin 3, gamma |

Key biomarker genes associated with oxidative metabolism [Ucp3, Pdk4, Cycs, Cox5a, Lpl] and oxidative myofibers [Mhc Ia, Mhc IIa], but not glycolytic myofibers [Mhc IIb] were induced by ERRγ in quadriceps of transgenic mice (FIG. 2B). Conversely, many of the biomarker genes [Ucp3, Cycs, AcscII, Cox6a2, Ppara] were found to be down-regulated by siRNA-mediated ERRγ knockdown in primary cultured myotubes (FIG. 2F) isolated from oxidative muscles (soleus and red gastrocnemius). Moreover, the oxidative changes were confirmed at the protein level as exemplified by increased expression of myoglobin, cytochrome c and UCP3 in transgenic relative to wild type muscle (FIG. 2C). Furthermore, staining of gastrocnemius cryo-sections for defining oxidative mitochondrial enzyme SDH activity revealed an increase in oxidative myofibers in ERRGO compared to wild type mice (FIG. 2D), which was confirmed by electron microscopy.

To access the metabolic effects of ERRγ at the cellular level, the mitochondrial bioenergetics were measured in wild type and ERRγ over-expressing C2C12 cells using an extracellular flux analyzer. Specifically, the oxygen consumption rate (OCR) (an indicator of mitochondrial respiration) along with the extracellular acidification rate (ECAR) (a measure of glycolysis) was determined in these cells (FIGS. 2G and H). ERRγ expression significantly induced mitochondrial respiration (OCR), reduced cellular glycolysis (ECAR) resulting in an 85% shift in the cellular energy production ratio towards oxidative phosphorylation (FIG. 2E).

These results show that ERRγ promotes an overt conversion of glycolytic fast-twitch muscles, such as quadriceps, to an oxidative slow-twitch phenotype.

EXAMPLE 5

ERRγ Promotes Skeletal Muscle Vascularization

Intrinsic vascularization of slow-twitch myofibers enables a baseline of exercise independent fatigue resistance. This example provides results demonstrating that ERRγ, by virtue of its restricted expression to type I fibers can, in addition to promoting oxidative metabolism, simultaneously induce vessel formation to match the increased oxidative demand.

Muscle cryo-sections were stained for PECAM 1 (CD31), an endothelial cell marker that is routinely used to detect angiogenesis and changes in tissue vasculature. Transgenic muscles showed increased PECAM 1 (FIG. 3A) staining compared to wild type. Similarly, transgenic muscle cryo-sections showed an increase in alkaline phosphatase staining, an alternative marker for tissue endothelium (FIG. 3B). These findings point indicated induction of angiogenesis and muscle vascularization by ERRγ.

To show that ERRγ supports formation of functional non-leaky blood vessels micro-angiography following intra-ventricular perfusion of a fluorescent microspheres (0.1 μM) was used. The impermeability of the microspheres allows their vascular retention, enabling confocal angiographic "vascular mapping" of intact and mature blood vessels. Examination of perfused microspheres in wild type and transgenic gastrocnemius revealed an increase in muscle vascularity by ERRγ (FIG. 3C) showing that ERRγ dually promotes oxidative fiber specification and neo-vascularization.

EXAMPLE 6

Paracrine Regulation of Muscle Vascularization of ERRγ

This example provides results showing how ERRγ expressed in myofibers can regulate proximal vascular development.

Figure 3J:
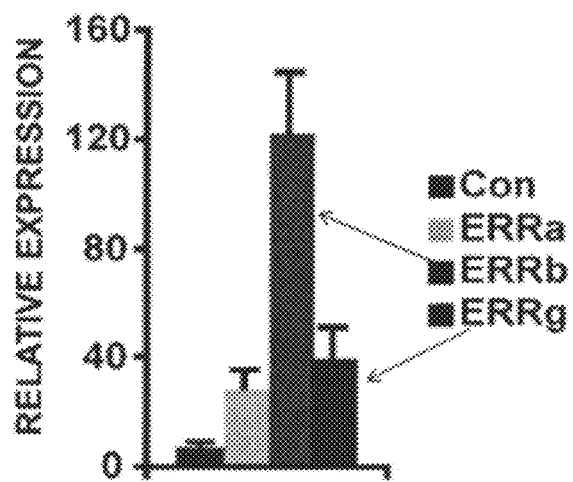
FIG. 3J shows that ERRγ activates Vegfa promoter. Vegfa gene 5' of the transcriptional start site containing promoter region was PCR cloned from mouse genomic DNA and sub-cloned up-stream of luciferase gene in pGL3 vector. All three isoforms of ERR (ERRα, ERRβ and ERRγ) transcriptionally activated Vegfa promoter.

Gene expression studies (FIG. 2A and Table 3) revealed increased expression of 25 angiogenic genes, including vascular endothelial growth factor A (Vegfa) in ERRGO quadriceps. Real time PCR confirmed induction of two Vegfa isoforms (165 & 189) along with Vegfb and Fgf1 in transgenic muscles (FIGS. 3D-H). Moreover, ERRγ as well as ERRα & ERRβ increased the transcription of a Vegfa promoter-driven luciferase reporter in AD 293 cells (FIG. 3J). In addition, the protein levels of Vegfa and Fgf1 were increased in the quadriceps of the transgenic mice (FIG. 3H), indicating that muscle ERRγ activates paracrine networks that are released into the microenvironment to promote neo-vascularization.

TABLE 3

Angiogenic genes up-regulated in the quadriceps of ERRγ transgenic mice as compared to wild type mice (N = 3, each pooled from 3 mice, $p < 0.05$, Bonferroni's multiple comparison test).

| Locus | Fold | Description |
|---|---|---|
| Cdh5 | 1.755 | cadherin 5 |
| Crhr2 | 2.072 | corticotropin releasing hormone receptor 2 |
| Cxcl12 | 2.05 | chemokine (C-X-C motif) ligand 12 |
| Efnb2 | 2.16 | ephrin B2 |
| Egfl7 | 1.958 | EGF-like domain 7 |
| Epas1 | 1.867 | endothelial PAS domain protein 1 |
| Fgf1 | 4.123 | fibroblast growth factor 1 |
| Flt1 | 1.85 | FMS-like tyrosine kinase 1 |
| Gja1 | 1.704 | gap junction membrane channel protein alpha 1 |
| Kdr | 1.718 | kinase insert domain protein receptor |
| Notch4 | 2.254 | Notch gene homolog 4 (*Drosophila*) |
| Nrp1 | 1.816 | neuropilin 1 |
| Pdgfrb | 1.895 | platelet derived growth factor receptor, beta polypeptide |
| Plcd1 | 2.009 | phospholipase C, delta 1 |
| Qk | 1.875 | quaking |
| Rhob | 1.702 | ras homolog gene family, member B |
| Sox17 | 1.98 | SRY-box containing gene 17 |
| Vegfa | 2.505 | vascular endothelial growth factor A |
| Vegfb | 2.341 | vascular endothelial growth factor B |
| Vezf1 | 1.958 | vascular endothelial zinc finger 1 |

As shown in Table 4, ERRγ also induces key transcriptional inducers of oxidative metabolism including Esrrb, Ppara, Ppard and Ppargc1b.

Table 4. Transcriptional regulators are targets of ERR' in the quadriceps of transgenic mice (N=3, each pooled from 3 mice, $p<0.05$, Bonferroni's multiple comparison test).

| LOCUS | DESCRIPTION | FOLD |
|---|---|---|
| Esrrb | estrogen related receptor, beta | 3 |
| Ppara | peroxisome proliferator activated receptor alpha | 2.444 |
| Ppard | peroxisome proliferator activator receptor delta | 2.065 |
| Ppargc1b | peroxisome proliferative activated receptor, gamma, coactivator 1 beta | 1.988 |

Figure 4A:
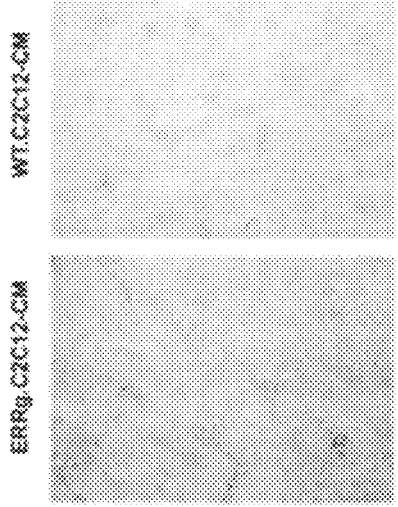
FIGS. 4A-E show paracrine stimulation of angiogenesis by ERRγ. (A) Tube formation in SVEC4-10 cells treated for 7-8 hr with conditioned media from WT and ERRγ over-expressing C2C12 myotubes. Similar results were obtained from 4-6 experiments. (B-D) Expression of Vegfa isoforms in WT and ERRγ over-expressing C2C12 myotubes (N=6). (E) Vegfa concentrations (pg/ml) in conditioned media from 2 day differentiated WT and ERRγ over-expressing C2C12 myotubes (N=3). Data in (B-E) are presented as mean±SD. * represents significant difference between WT and transgenic mice (p<0.05, unpaired Student's t-test).
Figures 4B, 4C:
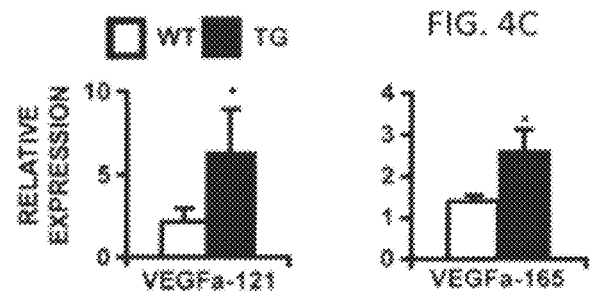
Figures 4D, 4E:
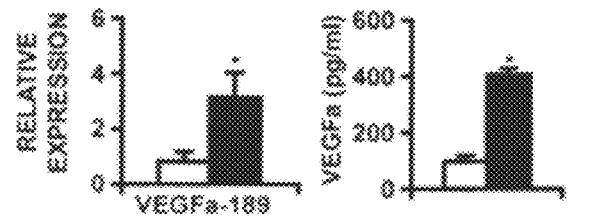

To directly test whether ERRγ triggers paracrine angiogenesis an SVEC4-10 (murine endothelial cells) tube formation assay was employed. It was reasoned that conditioned media from ERRγ over-expressing muscle cells would contain the appropriate signals to induce tube formation in endothelial cells. Indeed, treatment of SVEC4-10 cells with conditioned media from ERRγ over-expressing C2C12 myotubes stimulated tube formation in 7-8 hr (FIG. 4A). To confirm that the conditioned media contains angiogenic signals, the gene expression in cells and protein levels in the media (by ELISA) of a representative angiokine, Vegfa was examined. Overexpression of ERRγ in C2C12 myotubes increased expression of Vegfa-121, 165 and 189 genes (FIGS. 4B-D) and increases total Vegfa secretion (by 4-fold) in the media (FIG. 4E). These results demonstrate that ERRγ can induce angiogenic factors such as myocellular Vegfa to increase angiogenesis in a paracrine fashion.

EXAMPLE 7

Physiological Effects of ERRγ Remodeled Muscle

Aerobic exercise-induced remodeling of skeletal muscles depends on both an increase in oxidative capacity and new blood vessel formation; changes that are a critical part of the physiologic adaptation to training (Bloor, 2005; Egginton, 2008; Gavin et al.; 2007; Gustafsson and Kraus, 2001; Jensen et al., 2004; Waters et al., 2004). This example describes results showing the ability of ERRγ to promote physiological re-modeling.

Figure 5D:
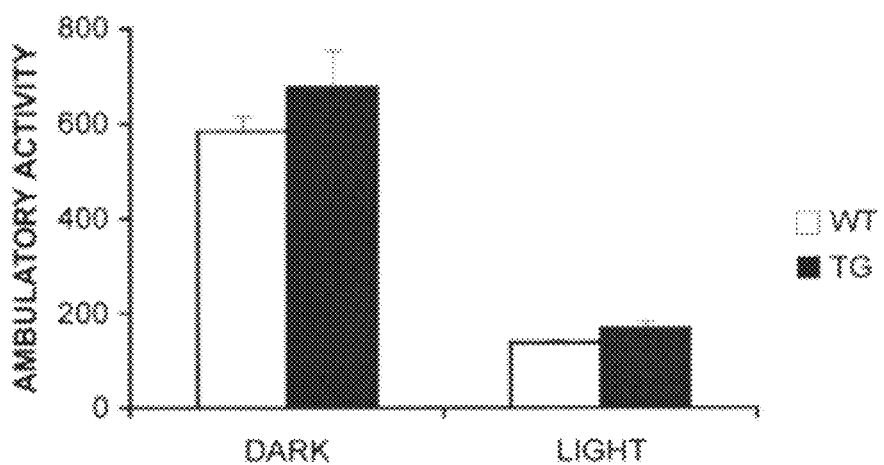

First, in metabolic cage oxymetric studies, the transgenic mice exhibited an increase in oxygen consumption (during both the light and dark cycles) in concert with the observed increased oxidative metabolism and blood supply to skeletal muscles (FIG. 5A). Second, the ERGGO mice have a lower Respiratory Exchange Ratio (RER) compared to the wild type mice indicative of a tendency to preferentially oxidize fat over carbohydrate in the transgenic skeletal muscles (FIG. 5B). The ambulatory activities of wild type and transgenic mice were comparable, and therefore unlikely to contribute to changes in oxymetric parameters (FIG. 5D).

Figure 5E:
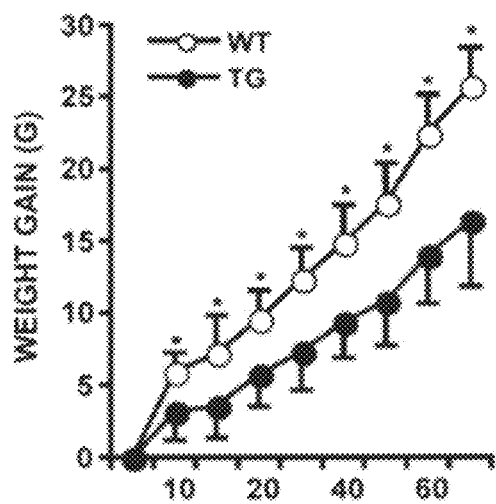

Based on these combined changes the ability of ERRGO mice to acquire enhanced running endurance was determined. ERRγ transgenic mice were able to run longer and further compared to the wild type littermates (FIG. 5C). Finally, the ERRGO mice were subjected to a high fat-high carbohydrate diet to establish whether the induction of endurance muscle and oxidative RER affected global metabolic balance. As expected ERRGO mice gained 35% less weight than wild type controls on a high fat diet (FIG. 5E).

These findings demonstrate that targeting of ERRγ increases oxidative metabolism and blood supply to skeletal muscle leading to increased oxygen consumption, better endurance and resistance to weight gain.

EXAMPLE 8

PGC1α-Independent Regulation of Aerobic Muscle by ERRγ

PGC1α is induced by hypoxia and exercise to promote HIF1α-independent vascularization of type II muscle (Arany et al., 2008) and further activated by post-translational modifications such as deacetylation (Jager et al., 2007; Puigserver et al., 2001; Rodgers et al., 2005). This example describes results showing that the ERRγ-induced changes in the muscle were due to the induction and/or activation of PGC1α.

Figure 6F:
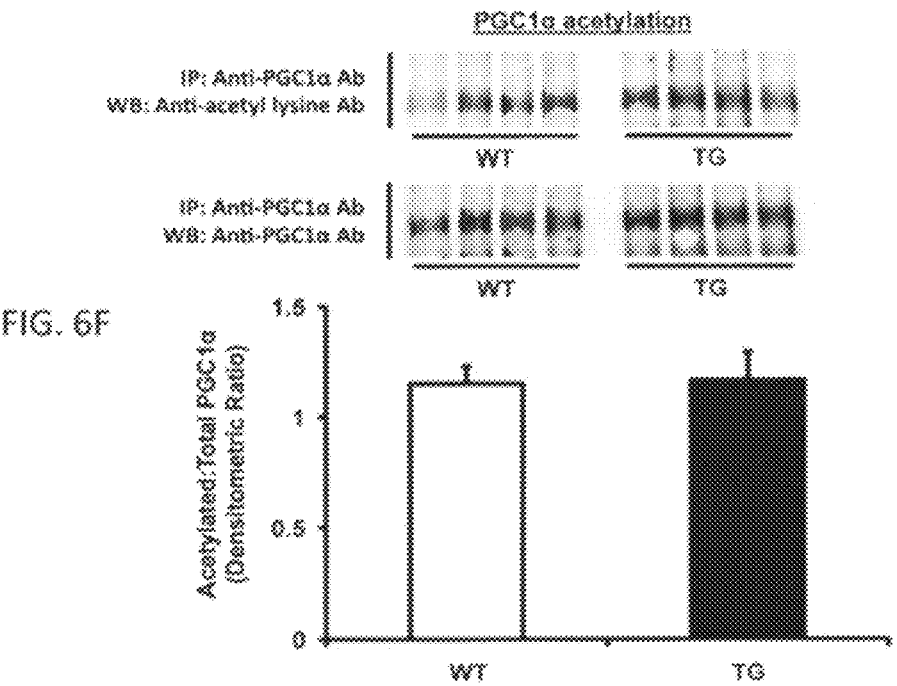

The levels of PGC1α mRNA, protein and acetylation remained unchanged in the ERRγ-transformed skeletal muscle (FIGS. 6A and 6F). Interestingly, of the two additional ERR isoforms that can mediate PGC1α signaling, ERRβ but not ERRα, was also significantly induced in transgenic muscle (Mootha et al., 2004; Schreiber et al., 2003; Huss et al., 2002).

Figure 6G:
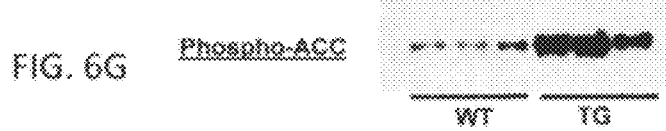
Figure 6H:
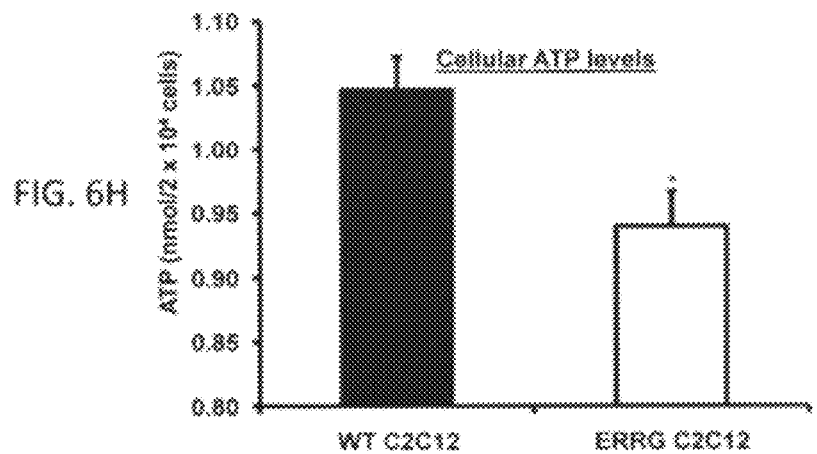

To determine if AMPK can ERRγ control metabolism, VEGF induction and vasculature remodeling in ERRGO mice in absence of enhanced PGC1α signaling, the following methods were used. AMPK is an alternative aerobic master-regulator, having a role in metabolic (Fujii et al., 2008; Fujii et al., 2007) and vascular adaptation (Zwetsloot et al., 2008). While AMPK is normally induced by exercise or hypoxia, it was surprisingly found to be constitutively activated in ERRGO muscle (FIGS. 6B and C). The AMPK activation was further validated by measuring phospho-ACC levels (an AMPK target and a bio-marker of AMPK activity), which was found to be higher in the transgenic compared to the wild type muscles (FIG. 6G). ATP consumption is critical to AMPK activation as AMP stimulates and ATP inhibits the enzyme (Xiao et al., 2007). Indeed, it was observed that ATP levels were lower in ERRγ over-expressing compared to control C2C12 muscle cells, providing a biochemical basis for the observed AMPK activation (FIG. 6H). (Note that cultured muscle cells were used for measuring ATP levels because ERRγ over-expression promotes both angiogenic gene expression as well as oxidative respiration in a fashion similar to transgenic muscle). Interestingly, in wild type mice, AMPK was more active in predominantly oxidative slow-twitch compared to predominantly glycolytic fast-twitch muscle, in resting state (FIGS. 6B and C). Indeed, a synthetic activator AICAR, at a dose (500 mg/kg/day) previously shown to stimulate AMPK in anaerobic muscle and improve aerobic performance (Narkar et al., 2008), was able to direct aspects of skeletal muscle transformation in a fashion similar to ERRγ (FIG. 6D).

These observations indicate a convergence between ERRγ and AMPK pathways that comprise an exercise-independent mechanism to direct intrinsic vascularization and oxidative metabolism in type I muscle, as depicted in FIG. 6E.

References

Alaynick et al., (2007). ERRgamma directs and maintains the transition to oxidative metabolism in the postnatal heart. Cell Metab 6, 13-24.

Annex et al., (1998). Induction and maintenance of increased VEGF protein by chronic motor nerve stimulation in skeletal muscle. Am J Physiol 274, H860-867.

Ao et al., (2008). Involvement of estrogen-related receptors in transcriptional response to hypoxia and growth of solid tumors. Proc Natl Acad Sci U S A 105, 7821-7826.

Arany et al., (2008). HIF-independent regulation of VEGF and angiogenesis by the transcriptional coactivator PGC-1alpha. Nature 451, 1008-1012.

Arany et al., (2007). The transcriptional coactivator PGC-1beta drives the formation of oxidative type IIX fibers in skeletal muscle. Cell Metab 5, 35-46.

Ariazi et al., (2002). Estrogen-related receptor alpha and estrogen-related receptor gamma associate with unfavorable and favorable biomarkers, respectively, in human breast cancer. Cancer Res 62, 6510-6518.

Baar et al., (2002). Adaptations of skeletal muscle to exercise: rapid increase in the transcriptional coactivator PGC-1. FASEB J 16, 1879-1886.

Bloor, C. M. (2005). Angiogenesis during exercise and training. Angiogenesis 8, 263-271.

Canto et al., (2010). Interdependence of AMPK and SIRT1 for metabolic adaptation to fasting and exercise in skeletal muscle. Cell Metab 11, 213-219.

Carmeliet, P. (2000). Mechanisms of angiogenesis and arteriogenesis. Nat Med 6, 389-395.

Cherwek et al., (2000). Fiber type-specific differential expression of angiogenic factors in response to chronic hindlimb ischemia. Am J Physiol Heart Circ Physiol 279, H932-938.

Cheung et al., (2005). Expression and functional study of estrogen receptor-related receptors in human prostatic cells and tissues. J Clin Endocrinol Metab 90, 1830-1844.

Dufour et al., (2007). Genome-wide orchestration of cardiac functions by the orphan nuclear receptors ERRalpha and gamma. Cell Metab 5, 345-356.

Dzamko et al., (2008). AMPK-independent pathways regulate skeletal muscle fatty acid oxidation. J Physiol 586, 5819-5831.

Egginton, S. (2008). Invited review: activity-induced angiogenesis. Pflugers Arch.

Ferrara, N., and Kerbel, R. S. (2005). Angiogenesis as a therapeutic target. Nature 438, 967-974.

Fluck, M., and Hoppeler, H. (2003). Molecular basis of skeletal muscle plasticity—from gene to form and function. Rev Physiol Biochem Pharmacol 146, 159-216.

Foo et al., (2006). Ephrin-B2 controls cell motility and adhesion during blood-vessel-wall assembly. Cell 124, 161-173.

Forough et al., (2006). Transcription factor Ets-1 regulates fibroblast growth factor-1-mediated angiogenesis in vivo: role of Ets-1 in the regulation of the PI3K/AKT/MMP-1 pathway. J Vasc Res 43, 327-337.

Fujii et al., (2000). Exercise induces isoform-specific increase in 5'AMP-activated protein kinase activity in human skeletal muscle. Biochem Biophys Res Commun 273, 1150-1155.

Fujii et al., (2008). Ablation of AMP-activated protein kinase alpha2 activity exacerbates insulin resistance induced by high-fat feeding of mice. Diabetes 57, 2958-2966.

Fujii et al., (2007). Role of AMP-activated protein kinase in exercise capacity, whole body glucose homeostasis, and glucose transport in skeletal muscle-insight from analysis of a transgenic mouse model. Diabetes Res Clin Pract 77 *Suppl* 1, S92-98.

Gao et al., (2006). Expression of estrogen receptor-related receptor isoforms and clinical significance in endometrial adenocarcinoma. Int J Gynecol Cancer 16, 827-833.

Gavin et al., (2007). No difference in the skeletal muscle angiogenic response to aerobic exercise training between young and aged men. J Physiol 585, 231-239.

Gerhart-Hines et al., (2007). Metabolic control of muscle mitochondrial function and fatty acid oxidation through SIRT1/PGC-1 alpha. EMBO J 26, 1913-1923.

Giguere, V. (2008). Transcriptional control of energy homeostasis by the estrogen-related receptors. Endocr Rev 29, 677-696.

Grunewald et al., (2006). VEGF-induced adult neovascularization: recruitment, retention, and role of accessory cells. Cell 124, 175-189.

Gupta et al., (1998). Chemokine receptors in human endothelial cells. Functional expression of CXCR4 and its transcriptional regulation by inflammatory cytokines. J Biol Chem 273, 4282-4287.

Gustafsson, T., and Kraus, W. E. (2001). Exercise-induced angiogenesis-related growth and transcription factors in skeletal muscle, and their modification in muscle pathology. Front Biosci 6, D75-89.

Hainaud et al., (2006). The role of the vascular endothelial growth factor-Delta-like 4 ligand/Notch4-ephrin B2 cascade in tumor vessel remodeling and endothelial cell functions. Cancer Res 66, 8501-8510.

Heard et al., (2000). Human ERRgamma, a third member of the estrogen receptor-related receptor (ERR) subfamily of orphan nuclear receptors: tissue-specific isoforms are expressed during development and in the adult. Mol Endocrinol 14, 382-392.

Hong, H., Yang, L., and Stallcup, M. R. (1999). Hormone-independent transcriptional activation and coactivator binding by novel orphan nuclear receptor ERR3. J Biol Chem 274, 22618-22626.

Hoppeler, H., and Vogt, M. (2001a). Hypoxia training for sea-level performance. Training high-living low. Adv Exp Med Biol 502, 61-73.

Hoppeler, H., and Vogt, M. (2001b). Muscle tissue adaptations to hypoxia. J Exp Biol 204, 3133-3139.

Huss et al., (2002). Peroxisome proliferator-activated receptor coactivator-1 alpha (PGC-1 alpha)coactivates the cardiac-enriched nuclear receptors estrogen-related receptor-alpha and -gamma. Identification of novel leucine-rich interaction motif within PGC-1 alpha. J Biol Chem 277, 40265-40274.

Huss et al., (2004). Estrogen-related receptor alpha directs peroxisome proliferator-activated receptor alpha signaling in the transcriptional control of energy metabolism in cardiac and skeletal muscle. Mol Cell Biol 24, 9079-9091.

Jager et al.,. (2007). AMP-activated protein kinase (AMPK) action in skeletal muscle via direct phosphorylation of PGC-1 alpha. Proc Natl Acad Sci U S A 104, 12017-12022.

Jensen et al., (2004). Effect of high intensity training on capillarization and presence of angiogenic factors in human skeletal muscle. J Physiol 557, 571-582.

Jensen et al., (2007). Possible CaMKK-dependent regulation of AMPK phosphorylation and glucose uptake at the onset of mild tetanic skeletal muscle contraction. Am J Physiol Endocrinol Metab 292, E1308-1317.

Johnson et al., (2004). Matrix metalloproteinase-9 is required for adequate angiogenic revascularization of ischemic tissues: potential role in capillary branching. Circ Res 94, 262-268.

Jorgensen et al., (2004). Knockout of the alpha2 but not alpha1 5'-AMP-activated protein kinase isoform abolishes 5-aminoimidazole-4-carboxamide-1-beta-4-ribofuranoside-but not contraction-induced glucose uptake in skeletal muscle. J Biol Chem 279, 1070-1079.

Lagouge et al., (2006). Resveratrol improves mitochondrial function and protects against metabolic disease by activating SIRT1 and PGC-1 alpha. Cell 127, 1109-1122.

Leon et al., (2002). Activated Notch4 inhibits angiogenesis: role of beta 1-integrin activation. Mol Cell Biol 22, 2830-2841.

Lin et al., (2002). Transcriptional co-activator PGC-1 alpha drives the formation of slow-twitch muscle fibres. Nature 418, 797-801.

Lin et al., (2004). Defects in adaptive energy metabolism with CNS-linked hyperactivity in PGC-1 alpha null mice. Cell 119, 121-135.

Mason et al., (2004). Loss of skeletal muscle HIF-1 alpha results in altered exercise endurance. PLoS Biol 2, e288.

Mason et al., (2007). HIF-1 alpha in endurance training: suppression of oxidative metabolism. Am J Physiol Regul Integr Comp Physiol 293, R2059-2069.

Matsui et al., (2006). Redundant roles of Sox17 and Sox18 in postnatal angiogenesis in mice. J Cell Sci 119, 3513-3526.

Minnich, A., Tian, N., Byan, L., and Bilder, G. (2001). A potent PPARalpha agonist stimulates mitochondrial fatty acid beta-oxidation in liver and skeletal muscle. Am J Physiol Endocrinol Metab 280, E270-279.

Mootha et al., (2004). Erralpha and Gabpa/b specify PGC-1 alpha-dependent oxidative phosphorylation gene expression that is altered in diabetic muscle. Proc Natl Acad Sci U S A 101, 6570-6575.

Muoio et al., (2002). Peroxisome proliferator-activated receptor-alpha regulates fatty acid utilization in primary human skeletal muscle cells. Diabetes 51, 901-909.

Muscat, G. E., and Kedes, L. (1987). Multiple 5'-flanking regions of the human alpha-skeletal actin gene synergistically modulate muscle-specific expression. Mol Cell Biol 7, 4089-4099.

Narkar et al., (2008). AMPK and PPARdelta agonists are exercise mimetics. Cell 134, 405-415.

Pajusola et al., (2005). Stabilized HIF-(alpha is superior to VEGF for angiogenesis in skeletal muscle via adeno-associated virus gene transfer. Faseb J 19, 1365-1367.

Partridge et al., (2000). Overexpression of a secretory form of FGF-1 promotes MMP-1-mediated endothelial cell migration. J Cell Biochem 78, 487-499.

Pette, D., and Staron, R. S. (2000). Myosin isoforms, muscle fiber types, and transitions. Microsc Res Tech 50, 500-509.

Pilegaard et al., (2003). Exercise induces transient transcriptional activation of the PGC-1 alpha gene in human skeletal muscle. J Physiol 546, 851-858.

Puigserver et al., (2001). Cytokine stimulation of energy expenditure through p38 MAP kinase activation of PPAR-gamma coactivator-1. Mol Cell 8, 971-982.

Ripoll et al., (1979). Changes in the capillarity of skeletal muscle in the growing rat. Pflugers Arch 380, 153-158.

Rockl (2007). Skeletal muscle adaptation to exercise training: AMP-activated protein kinase mediates muscle fiber type shift. Diabetes 56, 2062-2069.

Rodgers et al., (2005). Nutrient control of glucose homeostasis through a complex of PGC-1 alpha and SIRT1. Nature 434, 113-118.

Russell et al., (2003). Endurance training in humans leads to fiber type-specific increases in levels of peroxisome proliferator-activated receptor-gamma coactivator-1 and peroxisome proliferator-activated receptor-alpha in skeletal muscle. Diabetes 52, 2874-2881.

Russell et al., (2005). Regulation of metabolic transcriptional co-activators and transcription factors with acute exercise. FASEB J 19, 986-988.

Schreiber et al., (2003). The transcriptional coactivator PGC-1 regulates the expression and activity of the orphan nuclear receptor estrogen-related receptor alpha (ERRalpha). J Biol Chem 278, 9013-9018.

Seth et al., (2007). The transcriptional corepressor RIP140 regulates oxidative metabolism in skeletal muscle. Cell Metab 6, 236-245.

Shao et al., (2008). Statin and stromal cell-derived factor-1 additively promote angiogenesis by enhancement of progenitor cells incorporation into new vessels. Stem Cells 26, 1376-1384.

Springer et al., (1998). VEGF gene delivery to muscle: potential role for vasculogenesis in adults. Mol Cell 2, 549-558.

Springer et al., (2000). Angiogenesis monitored by perfusion with a space-filling microbead suspension. Mol Ther 1, 82-87.

Wang, Y. X., Zhang, C. L., Yu, R. T., Cho, H. K., Nelson, M. C., Bayuga-Ocampo, C. R., Ham, J., Kang, H., and Evans, R. M. (2004). Regulation of muscle fiber type and running endurance by PPARdelta. PLoS Biol 2, e294.

Waters et al., (2004). Voluntary running induces fiber type-specific angiogenesis in mouse skeletal muscle. Am J Physiol Cell Physiol 287, C1342-1348.

Winder, W. W., and Hardie, D. G. (1996). Inactivation of acetyl-CoA carboxylase and activation of AMP-activated protein kinase in muscle during exercise. Am J Physiol 270, E299-304.

Wojtaszewski et al., (2000). Isoform-specific and exercise intensity-dependent activation of 5'-AMP-activated protein kinase in human skeletal muscle. J Physiol 528 Pt 1, 221-226.

Xiao et al., (2007). Structural basis for AMP binding to mammalian AMP-activated protein kinase. Nature 449, 496-500.

Zechner, et al., (2010). Total skeletal muscle PGC-1 deficiency uncouples mitochondrial derangements from fiber type determination and insulin sensitivity. Cell Metab 12, 633-642.

Zhang et al., (2006). Estrogen-related receptors stimulate pyruvate dehydrogenase kinase isoform 4 gene expression. J Biol Chem 281, 39897-39906.

Zheng et al., H. (2007). Migration of endothelial progenitor cells mediated by stromal cell-derived factor-1 alpha/CXCR4 via PI3K/Akt/eNOS signal transduction pathway. J Cardiovasc Pharmacol 50, 274-280.

Zwetsloot et al., (2008). AMPK regulates basal skeletal muscle capillarization and VEGF expression, but is not necessary for the angiogenic response to exercise. J Physiol 586, 6021-6035.

In view of the many possible embodiments to which the principles of the disclosure may be applied, it should be recognized that the illustrated embodiments are only examples of the disclosure and should not be taken as limiting the scope of the invention. Rather, the scope of the invention is defined by the following claims. We therefore claim as our invention all that comes within the scope and spirit of these claims.

We claim:

1. A method of increasing vascularization in a mammal's skeletal muscle, comprising:

administering a therapeutically effective amount of one or more agents that increases estrogen-related receptor gamma (ERRγ) activity to a mammal, wherein the one or more agents that increases ERRγ activity is

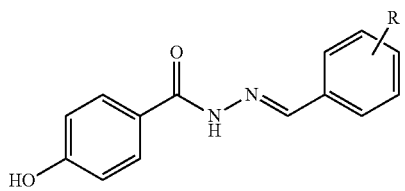

wherein R is H (DY162), p-CH$_3$ (DY163), 2-Cl, 3-CF$_3$ (DY165), p-CF$_3$ (DY168), p-OCH$_3$(DY169), 3-NO$_2$, 4CF$_3$ (DY170), 2,3-O$_2$CH$_3$ (DY174), or m-CH$_3$ (DY159),

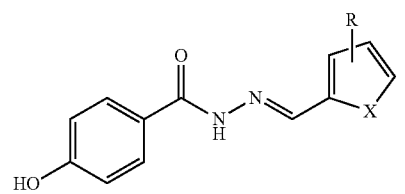

wherein X is S and R is 5-CH$_3$ (DY166), 5-CH$_2$CH$_3$ (DY164), or 5-NO$_2$ (DY167);
wherein X is O and R is 4,5-CH$_3$ (DY173) or CH$_2$CH$_3$ (DY175), or wherein X is CH, and R is 2-Cl, 3-CF$_3$, p-CF$_3$; p-OCH$_3$, 3-NO$_2$, 4-CF$_3$; or 2,3-O$_2$CH$_3$;

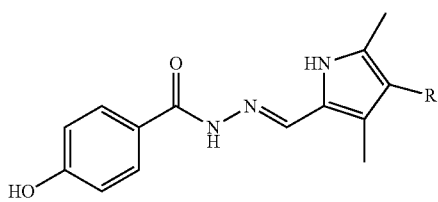

wherein R is H (DY117) or R is Br (DY172),

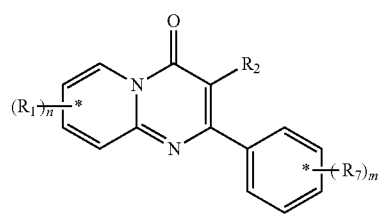

wherein
m is 0, 1 or 2;
n is 0, 1 or 2;
R$_1$ and R$_7$ are independently selected from
1) H;
2) Halo;
3) OH;

4) (C=O)$_a$,O$_b$C$_1$-C$_4$ alkyl, wherein a is 0 or 1 and b is 0 or 1, wherein the alkyl can be substituted by 0, 1 or more substituted groups independently selected from H or C$_3$C$_6$ heterocyclyl;
5) (C=O), O$_b$C$_3$-C$_6$ cycloalkyl, wherein a is 0 or 1 and b is 0 or 1;
R2 is selected from:
1) H;
2) C$_1$-C$_3$ alkyl, wherein the alkyl can be substituted by 0, 1 or more substituted groups independently selected from H or C$_3$C$_6$ heterocyclyl;
3) C$_3$-C$_6$ cycloalkyl;

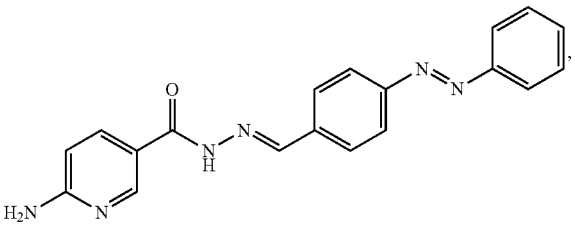

or combinations thereof; and
not exercising the mammal, wherein the mammal has muscle atrophy due to sarcopenia, cachexia, being bedridden, being confined to a wheelchair, having had a limb in a cast, cancer, AIDS, congestive heart failure, chronic obstructive pulmonary disease, renal failure, a severe burn, Dejerine Sottas syndrome (HSMN Type III), weightlessness, liver failure, starvation, disuse, or muscular dystrophy.

2. The method of claim 1, wherein the method further comprises:
selecting the mammal having muscle atrophy due to sarcopenia, cachexia, being bedridden, being confined to a wheelchair, having had a limb in a cast, cancer, AIDS, congestive heart failure, chronic obstructive pulmonary disease, renal failure, a severe burn, Dejerine Sottas syndrome (HSMN Type III), weightlessness, liver failure, starvation, disuse, or muscular dystrophy.

3. The method of claim 1, wherein the mammal is a human.

4. The method of claim 1, wherein the ERRγ agonist is DY131, GSK4716, or combinations thereof.

5. A method of increasing vascularization in a mammal's skeletal muscle by at least 25%, comprising:
administering a therapeutically effective amount of one or more agents that increases ERRγ activity to a mammal, wherein the one or more agents that increases ERRγ activity is

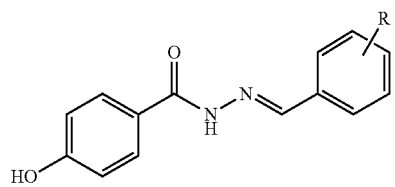

wherein R is H (DY162), p-CH$_3$ (DY163), 2-Cl, 3-CF$_3$ (DY165), p-CF$_3$ (DY168), p-OCH$_3$(DY169), 3-NO$_2$, 4CF$_3$ (DY170), 2,3-O$_2$CH$_3$ (DY174), or m-CH$_3$ (DY159),

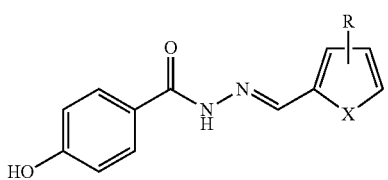

wherein X is S and R is 5-CH$_3$ (DY166), 5-CH$_2$CH$_3$ (DY164), or 5-NO$_2$ (DY167);

wherein X is O and R is 4,5-CH$_3$ (DY173) or CH$_2$CH$_3$ (DY175), or wherein X is CH, and R is 2-Cl, 3-CF$_3$, p-CF$_3$; p-OCH$_3$, 3-NO$_2$, 4-CF$_3$; or 2,3-O$_2$CH$_3$;

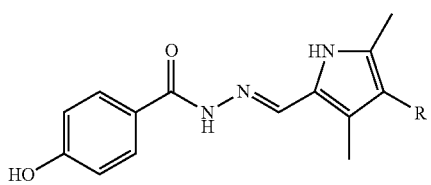

wherein R is H (DY117) or R is Br (DY172),

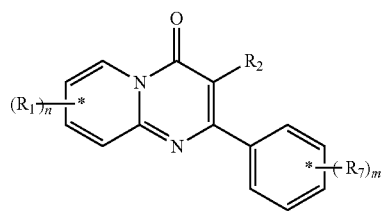

wherein
m is 0, 1 or 2;
n is 0, 1 or 2;
R$_1$ and R$_7$ are independently selected from
1) H;
2) Halo;
3) OH;
4) (C=O)$_a$,O$_b$C$_1$C$_4$ alkyl, wherein a is 0 or 1 and b is 0 or 1, wherein the alkyl can be substituted by 0, 1 or more substituted groups independently selected from H or C$_3$C$_6$ heterocyclyl;
5) (C=O)$_a$O$_b$C$_3$-C$_6$ cycloalkyl, wherein a is 0 or 1 and b is 0 or 1;
R2 is selected from:
1) H;
2) C$_1$-C$_3$ alkyl, wherein the alkyl can be substituted by 0, 1 or more substituted groups independently selected from H or C$_3$C$_6$ heterocyclyl;
3) C$_3$-C$_6$ cycloalkyl;

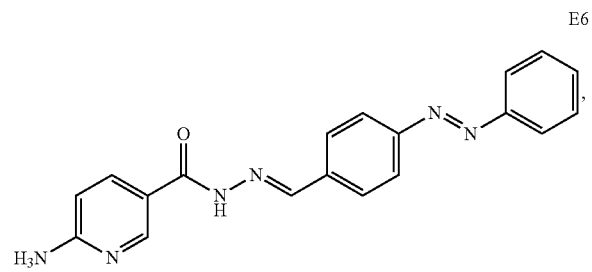 [SMILES: Nc1ccc(C(=O)N/N=C/c2ccc(/N=N/c3ccccc3)cc2)cn1]

or combinations thereof; and not exercising the mammal, wherein the mammal has muscle atrophy due to sarcopenia, cachexia, is bedridden, is confined to a wheelchair, had a limb in a cast, cancer, AIDS, congestive heart failure, chronic obstructive pulmonary disease, renal failure, a severe burn, Dejerine Sottas syndrome (HSMN Type III), weightlessness, liver failure, starvation, disuse, or muscular dystrophy, and wherein the increase of at least 25% is relative to an amount of vascularization in the absence of administration of the one or more agents that increases ERRγ activity.

6. A method of enhancing muscle rehabilitation or muscle performance in a mammal, comprising:

administering a therapeutically effective amount of one or more agents that increases ERRγ activity to a mammal, wherein the one or more agents that increases ERRγ activity is

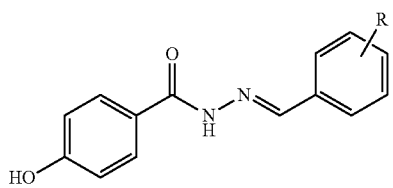

wherein R is H (DY162), p-CH$_3$ (DY163), 2-Cl, 3-CF$_3$ (DY165), p-CF$_3$ (DY168), p-OCH$_3$(DY169), 3-NO$_2$, 4CF$_3$ (DY170), 2,3-O$_2$CH$_3$ (DY174), or m-CH$_3$ (DY159),

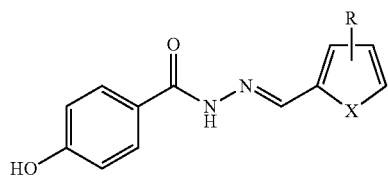

wherein X is S and R is 5-CH$_3$ (DY166), 5-CH$_2$CH$_3$ (DY164), or 5-NO$_2$ (DY167);

wherein X is O and R is 4,5-CH$_3$ (DY173) or CH$_2$CH$_3$ (DY175), or whereinX is CH, and R is 2-Cl, 3-CF$_3$ p-CF$_3$; p-OCH$_3$, 3-NO$_2$, 4-CF$_3$; or 2,3-O$_2$CH$_3$;

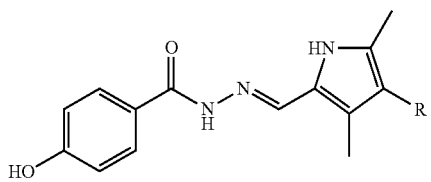

wherein R is H (DY117) or R is Br (DY172),

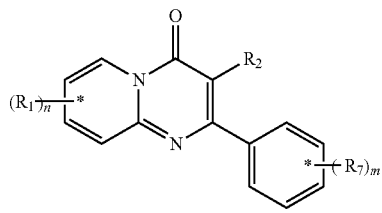

wherein
  m is 0, 1 or 2;
  n is 0, 1 or 2;
  $R_1$ and $R_7$ are independently selected from
    1) H;
    2) Halo;
    3) OH;
    4) $(C=O)_a, O_b C_1 C_4$ alkyl, wherein a is 0 or 1 and b is 0 or 1, wherein the alkyl can be substituted by 0, 1 or more substituted groups independently selected from H or $C_3 C_6$ heterocyclyl;
    5) (C=O), $O_b C_3$-$C_6$ cycloalkyl, wherein a is 0 or 1 and b is 0 or 1;
  R2 is selected from:
    1) H;
    2) $C_1$-$C_3$ alkyl, wherein the alkyl can be substituted by 0, 1 or more substituted groups independently selected from H or $C_3 C_6$ heterocyclyl;
    3) $C_3$-$C_6$ cycloalkyl;

E6

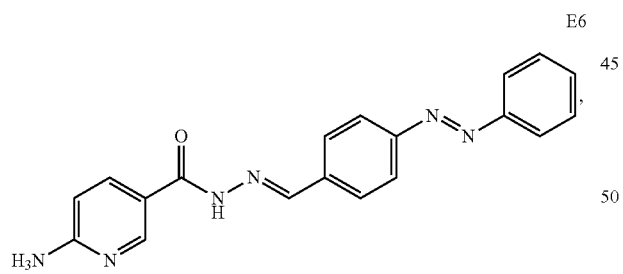

or combinations thereof; and
not exercising the mammal,
  wherein the mammal has muscle atrophy due to sarcopenia, cachexia, is bedridden, is confined to a wheelchair, had a limb in a cast, cancer, AIDS, congestive heart failure, chronic obstructive pulmonary disease, renal failure, a severe burn, Dejerine Sottas syndrome (HSMN Type III), weightlessness, liver failure, starvation, disuse, or muscular dystrophy, and
  wherein muscle rehabilitation or muscle performance is enhanced when running endurance of the muscle is increased as measured by a treadmill test, creatine kinase level is increased in the blood, electrical activity in the muscle is increased as measured by electromyography, or elasticity of the muscle is increased as measured by elastography.

7. A method of enhancing muscle rehabilitation or muscle performance in a mammal by at least 25%, comprising:
  administering a therapeutically effective amount of one or more agents that increases ERRγ activity to a mammal, wherein the one or more agents that increases ERRγ activity is

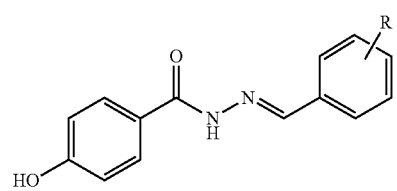

wherein R is H (DY162), p-$CH_3$ (DY163), 3-$CF_3$ (DY165), p-$CF_3$ (DY168), p-$OCH_3$ (DY169), 3-$NO_2$, 4$CF_3$ (DY170), 2,3-$O_2 CH_3$ (DY174), or m-$CH_3$ (DY159),

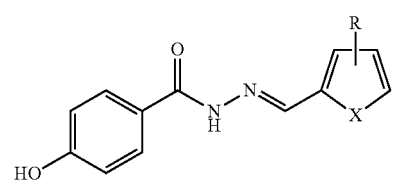

swherein X is S and R is 5-$CH_3$ (DY166), 5-$CH_2 CH_3$ (DY164), or 5-$NO_2$ (DY167); wherein X is O and R is 4,5-$CH_3$ (DY173) or $CH_2 CH_3$ (DY175), or wherein X is CH, and R is 2-Cl, 3-$CF_3$, p-$CF_3$; p-$OCH_3$, 3-$NO_2$, 4-$CF_3$; or 2,3-$O_2 CH_3$;

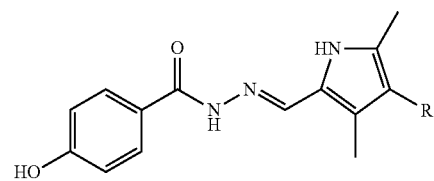

wherein R is H (DY117) or R is Br (DY172),

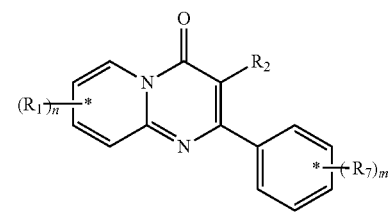

wherein
  m is 0, 1 or 2;
  n is 0, 1 or 2;
  $R_1$ and $R_7$ are independently selected from
    1) H;
    2) Halo;
    3) OH;

4) (C=O)$_a$, O$_b$C$_1$-C$_4$ alkyl, wherein a is 0 or 1 and b is 0 or 1, wherein the alkyl can be substituted by 0, 1 or more substituted groups independently selected from H or C$_3$-C$_6$ heterocyclyl;

5) (C=O), O$_b$C$_3$-C$_6$ cycloalkyl, wherein a is 0 or 1 and b is 0 or 1;

R2 is selected from:
1) H;
2) C$_1$-C$_3$ alkyl, wherein the alkyl can be substituted by 0, 1 or more substituted groups independently selected from H or C$_3$C$_6$ heterocyclyl;
3) C$_3$-C$_6$ cycloalkyl;

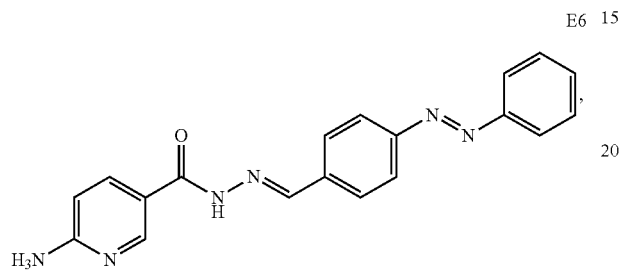

E6 or combinations thereof; and
not exercising the mammal,
wherein the mammal has muscle atrophy due to sarcopenia, cachexia, is bedridden, is confined to a wheelchair, had a limb in a cast, cancer, AIDS, congestive heart failure, chronic obstructive pulmonary disease, renal failure, a severe burn, Dejerine Sottas syndrome (HSMN Type III), weightlessness, liver failure, starvation, disuse, or muscular dystrophy,
wherein muscle performance is enhanced when running endurance of the muscle is increased by at least 25% as measured by a treadmill test, creatine kinase level is increased in the blood by at least 25%, electrical activity in the muscle is increased by at least 25% as measured by electromyography, or elasticity of the muscle is increased by at least 25% as measured by elastography, and
wherein the increase of at least 25% is relative to an amount of muscle performance in the absence of administration of the one or more agents that increases ERRγ activity.

8. The method of claim 1, wherein the mammal is a human that has muscular dystrophy.

9. The method of claim 1, wherein the mammal is a human having muscle atrophy due to sarcopenia.

10. The method of claim 1, wherein the mammal is a human having muscle atrophy due to being bedridden or being confined to a wheelchair.

11. The method of claim 1, wherein the mammal is a human that has AIDS.

12. The method of claim 1, wherein the mammal is a human that has congestive heart failure.

13. The method of claim 1, wherein the mammal is a human that has chronic obstructive pulmonary disease.

14. The method of claim 1, wherein the mammal is a human that has renal failure.

15. The method of claim 1, wherein the mammal is a human that has liver failure.

16. The method of claim 1, wherein the mammal is a human that has muscle atrophy due to experiencing a period of weightlessness.

17. The method of claim 1, wherein the mammal is a human that has muscle atrophy due to disuse.

18. The method of claim 1, wherein the one or more agents that increases ERRγ activity is:

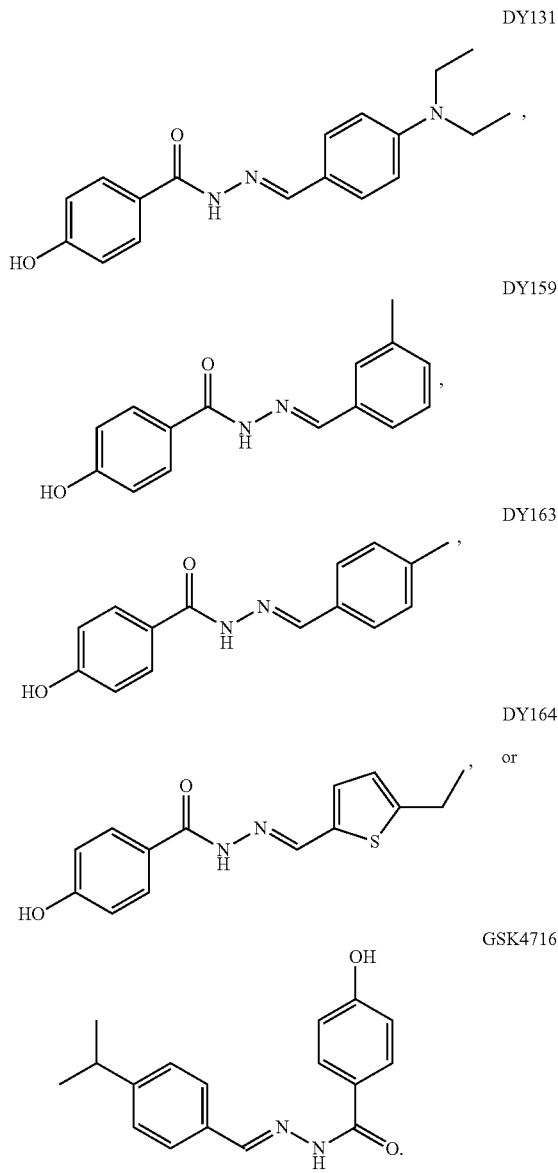

* * * * *